United States Patent
Liu et al.

(10) Patent No.: US 11,508,484 B1
(45) Date of Patent: Nov. 22, 2022

(54) PREDICTION OF RESPIRATORY THERAPY COMPLIANCE

(71) Applicant: ResMed Pty Ltd, Bella Vista (AU)

(72) Inventors: Nathan Liu, Sydney (AU); Sakeena De Souza, Sydney (AU); Oleksandr Gromenko, Singapore (MY)

(73) Assignee: ResMed Pty Ltd, Bella Vista (AU)

( * ) Notice: Subject to any disclaimer, the term of this patent is extended or adjusted under 35 U.S.C. 154(b) by 210 days.

(21) Appl. No.: 16/723,089

(22) Filed: Dec. 20, 2019

Related U.S. Application Data

(60) Provisional application No. 62/786,225, filed on Dec. 28, 2018.

(51) Int. Cl.
    G16H 50/30    (2018.01)
    G16H 10/60    (2018.01)
    A61M 16/06    (2006.01)

(52) U.S. Cl.
     CPC ........ *G16H 50/30* (2018.01); *A61M 16/0616* (2014.02); *G16H 10/60* (2018.01); *A61M 2202/0208* (2013.01)

(58) Field of Classification Search
     CPC ........ G16H 20/40; G16H 40/60; G16H 50/30; G16H 10/60; A61M 16/0616; A61M 2202/0208; A61M 16/0066; A61M 16/0051; A61M 16/024; A61M 16/06; A61B 5/4833; A61B 5/0816; A61B 5/1077; G06N 20/10
     USPC ........................................................ 705/2, 3
     See application file for complete search history.

(56) References Cited

U.S. PATENT DOCUMENTS

| | | | |
|---|---|---|---|
| 4,782,832 A | 11/1988 | Trimble | |
| 4,944,310 A | 7/1990 | Sullivan | |
| 6,532,959 B1 | 3/2003 | Berthon-Jones | |
| 6,581,594 B1 | 6/2003 | Drew | |
| 8,200,510 B1 * | 6/2012 | Berger | G16H 10/20 705/3 |
| 8,333,696 B2 * | 12/2012 | Levendowski | G16H 50/50 128/920 |
| 8,634,900 B2 | 1/2014 | Smith | |

(Continued)

FOREIGN PATENT DOCUMENTS

| | | | | |
|---|---|---|---|---|
| AU | 2005314415 A1 * | 7/2007 | ....... | A61B 17/12104 |
| AU | 2010201032 A1 * | 11/2010 | ....... | A61B 5/08 |

(Continued)

OTHER PUBLICATIONS

Ghosh et al., Identifying poor compliance with CPAP in obstructive sleep apnoea: A simple prediction equation using data after a two week trial, Respiratory Medicine (2013) 107, p. 936-942 (Year: 2013).*

(Continued)

*Primary Examiner* — Jason S Tiedeman
(74) *Attorney, Agent, or Firm* — Nixon Peabody LLP

(57) ABSTRACT

Systems and methods have been developed to increase user compliance and adherence to respiratory therapy devices. For instance, in some examples the disclosed technology may monitor usage data output from a respiratory therapy device to determine, based on the trends of usage, when a user is likely to terminate or reduce usage within a specified time window. Flagging a user may also trigger further actions to automatically intervene before the user terminates engagement with the service.

31 Claims, 20 Drawing Sheets

(56) References Cited

U.S. PATENT DOCUMENTS

| | | | |
|---|---|---|---|
| 2006/0178590 A1* | 8/2006 | Hebblewhite | A61B 5/08 600/529 |
| 2008/0161651 A1* | 7/2008 | Peterson | G16H 10/60 600/300 |
| 2009/0044808 A1 | 2/2009 | Guney | |
| 2009/0050156 A1 | 2/2009 | Ng | |
| 2009/0107498 A1 | 4/2009 | Plattner et al. | |
| 2010/0000534 A1 | 1/2010 | Kooij | |
| 2010/0205008 A1* | 8/2010 | Hua | G06Q 50/22 705/3 |
| 2014/0373374 A1 | 12/2014 | Znamenskiy et al. | |
| 2015/0148617 A1* | 5/2015 | Friedman | G16H 40/63 600/301 |
| 2015/0154380 A1 | 6/2015 | Duckworth et al. | |
| 2015/0286333 A1 | 10/2015 | Shey | |
| 2015/0290406 A1 | 10/2015 | Bertinetti | |
| 2016/0174903 A1 | 6/2016 | Cutaia | |
| 2016/0184538 A1 | 6/2016 | Grashow | |
| 2016/0193437 A1* | 7/2016 | Bao | A45C 3/001 128/203.14 |
| 2016/0270718 A1* | 9/2016 | Heneghan | G16H 50/20 |
| 2017/0196500 A1* | 7/2017 | Wysoski | A61B 5/7278 |
| 2017/0209657 A1* | 7/2017 | Levings | A61M 16/0066 |
| 2017/0266408 A1 | 9/2017 | Giovannelli et al. | |
| 2018/0178055 A1 | 6/2018 | Netter | |
| 2018/0199882 A1 | 7/2018 | Klee et al. | |
| 2018/0236191 A1 | 8/2018 | Martin | |
| 2018/0317859 A1* | 11/2018 | Kohli | A61B 5/0022 |
| 2019/0167141 A1* | 6/2019 | Duckert | G16H 40/67 |
| 2021/0044489 A1* | 2/2021 | Li | H04L 41/147 |
| 2021/0154422 A1* | 5/2021 | Hisahara | G16H 15/00 |

FOREIGN PATENT DOCUMENTS

| | | | | |
|---|---|---|---|---|
| AU | 2013274976 A1 * | 1/2015 | | G16H 10/20 |
| CA | 3066632 A1 * | 12/2018 | | A61B 5/0205 |
| CN | 108474841 A | 8/2018 | | |
| EP | 2542287 B1 | 12/2015 | | |
| WO | 1998004310 A1 | 2/1998 | | |
| WO | 1998034665 A1 | 8/1998 | | |
| WO | 2000078381 A1 | 12/2000 | | |
| WO | 2006074513 A1 | 7/2006 | | |
| WO | 2010135785 A1 | 12/2010 | | |
| WO | WO-2015191562 A1 * | 12/2015 | | G06F 19/3418 |
| WO | WO-2016192941 A1 * | 12/2016 | | A61B 5/4818 |
| WO | WO 2018/007997 A | 1/2018 | | |

OTHER PUBLICATIONS

Baratta et al., Long-term prediction of adherence to continuous positive air pressure therapy for the treatment of moderate/severe obstructive sleep apnea syndrome, Sleep Medicine 43 (2018) 66-70 (Year: 2018).*

Wolkove et al., Long-term compliance with continuous positive airway pressure in patients with obstructive sleep apnea, Can Respir J 2008;15(7):365-369. (Year: 2008).*

Law et al., Depression May Reduce Adherence during CPAP Titration Trial, Journal of Clinical Sleep Medicine, vol. 10, No. 2, 2014, pp. 163-169 (Year: 2014).*

Rafael-Palou et al., Comparative analysis of predictive methods for early assessment of compliance with continuous positive airway pressure therapy, BMC Medical Informatics and Decision Making (2018) 18:81, 14 pages (Year: 2018).*

West, John B., Respiratory Physiology: The Essentials, Ninth Edition, 2012, Wolters Kulwer | Lippincott Williams & Wilkins (210 pages).

Varendh, et al., PAP treatment in patients with OSA does not induce long-term nasal obstruction; Journal of Sleep Research; J Sleep Res. 2018; e12768; pp. 1-10; https://doi.org/10.1111/jsr.12768.

Engaging sleep apnea patients in their own care; PHILIPS Innovation DreamMapper; 2018 Koninklijke Philips N.V.; 2 pgs.; www.phillips.com; http://www.dreammapper.com.

Engaging sleep apnea patients in their own care—Case study | Philips; PHILIPS; Nov. 14, 2018; 7 pgs., https://www.philips.com/a-w/about/news/archive/case-studies/20180830-engaging-sleep-apnea-patients-in-their-own-care.html.

Spotlight: Predicting Daily CPAP Compliance; respiratory:tech by Somnoware; Nov. 14, 2018; 6 pgs.; https://www.somnoware.com/blog/spotlight-predicting-cpap-compliance-by-patient-population.

PAP Therapy Management Mobile Apps; May 2017; 2 pgs.; sleepreviewingmag.com.

Rafael-Palou et al., "Comparative analysis of predictive methods for early assessment of compliance with continuous positive airway pressure therapy," BMC Medical Informatics Decision Making, vol. 18, No. 81, Publication [online]. Sep. 18, 2018, pp. 1-27.

International Search Report and Written Opinion in International Patent Application No. PCT/US2019/068375 dated Mar. 12, 2020 (16 pages).

Extended European Search Report for EP Application No. 19903613.8, dated Aug. 22, 2022.

* cited by examiner

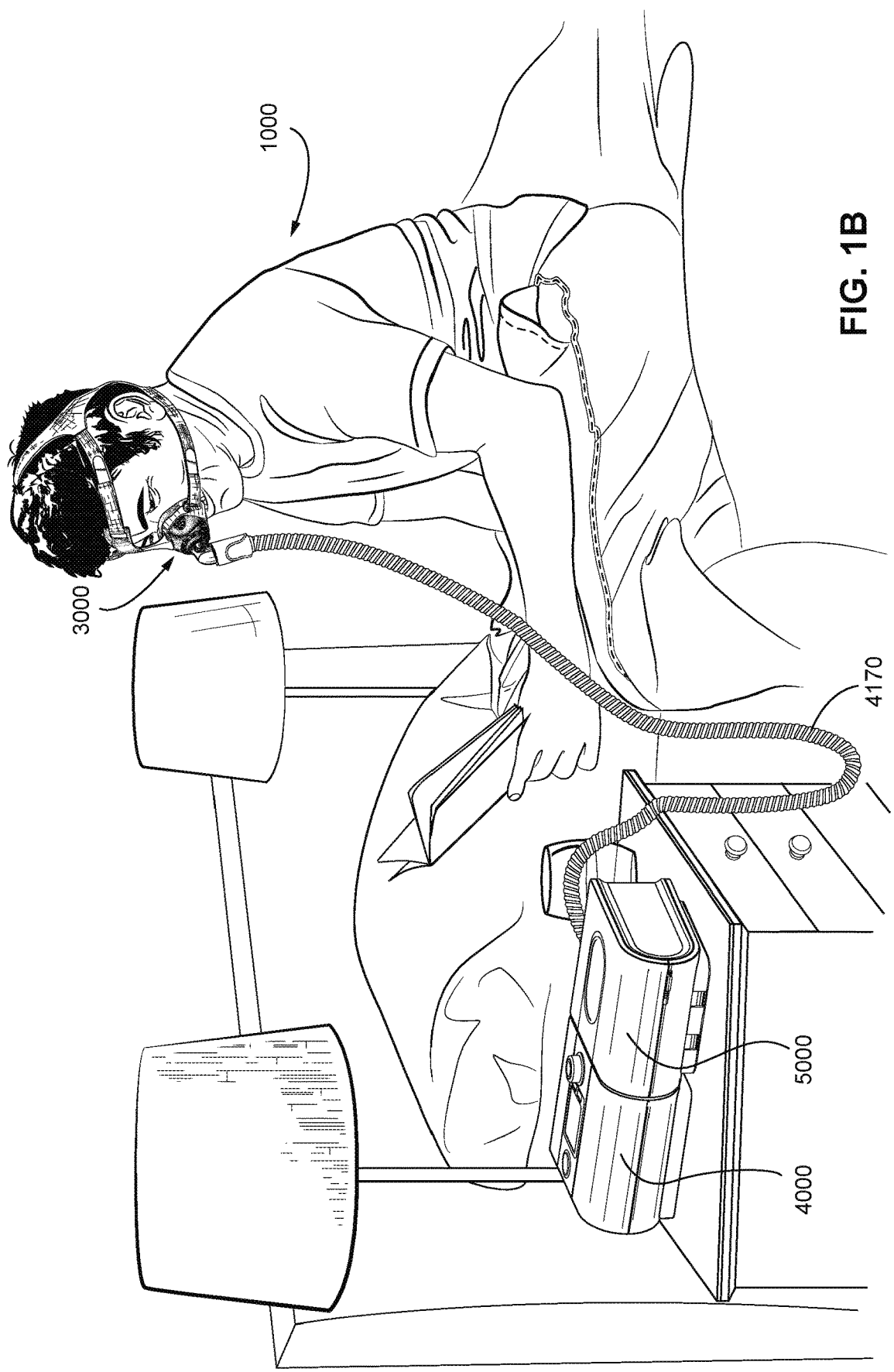

PREDICTION OF RESPIRATORY THERAPY COMPLIANCE

1 CROSS REFERENCE TO RELATED APPLICATIONS

This application claims priority to U.S. Provisional Application No. 62/786,225, filed Dec. 28, 2018, titled PREDICTION OR RESPIRATORY THERAPY COMPLIANCE, the contents of which are incorporated herein by reference.

2 BACKGROUND OF THE TECHNOLOGY

2.1 Field of the Technology

The present technology also relates to the prediction of compliance, usage, or quitting of usage of respiratory therapy devices.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient CO2 to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various therapies, such as Continuous Positive Airway Pressure (CPAP) therapy, Non-invasive ventilation (NIV) and Invasive ventilation (IV) have been used to treat one or more of the above respiratory disorders.

2.2.2.1 Respiratory Pressure Therapies

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.2.2 Flow Therapies

Not all respiratory therapies aim to deliver a prescribed therapy pressure. Some respiratory therapies aim to deliver a prescribed respiratory volume, possibly by targeting a flow rate profile over a targeted duration. In other cases, the interface to the patient's airways is 'open' (unsealed) and the respiratory therapy may only supplement the patient's own spontaneous breathing. In one example, High Flow therapy (HFT) is the provision of a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate. HFT has been used to treat OSA, CSR, COPD and other respiratory disorders. One mechanism of action is that the high flow rate of air at the airway entrance improves ventilation efficiency by flushing, or washing out, expired CO2 from the patient's anatomical deadspace. HFT is thus sometimes referred to as a deadspace therapy (DST). In other flow therapies, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched gas at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen.

2.2.3 Treatment Systems

These respiratory therapies may be provided by a therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

Another form of therapy system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include CPAP devices and ventilators. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 $cmH_2O$).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks
(ISO 17510-2:2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |

-continued

Table of noise of prior masks
(ISO 17510-2:2007, 10 cmH₂O pressure at 1 m)

| Mask name | Mask type | A-weighted sound power level dB(A) (uncertainty) | A-weighted sound pressure dB(A) (uncertainty) | Year (approx.) |
|---|---|---|---|---|
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 cmH₂O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular, it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of one form of the present technology is to determine the likelihood a user t using a respiratory therapy device will quit within a specified time window.

Another aspect of one form of the present technology is identifying, for a user using a respiratory therapy device, the weekly trend of the number of non-usage days, average usage per day, and standard deviation of usage to determine whether the user will quit or reduce usage.

Another aspect of one form of the present technology is processing usage data output from a respiratory therapy device using a random forest and logistical regression algorithm to determine whether a user will quit within a specified time window (e.g. two weeks, one week, or three weeks).

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

FIG. 2A shows an overview of a human respiratory system including the nasal and oral cavities, the larynx, vocal folds, oesophagus, trachea, bronchus, lung, alveolar sacs, heart and diaphragm.

4.3 Patient Interface

FIG. 3A shows a patient interface in the form of a nasal mask in accordance with one form of the present technology.

4.4 RPT Device

FIG. 4A shows an exploded view of an RPT device in accordance with one form of the present technology.

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

Figure 5A:
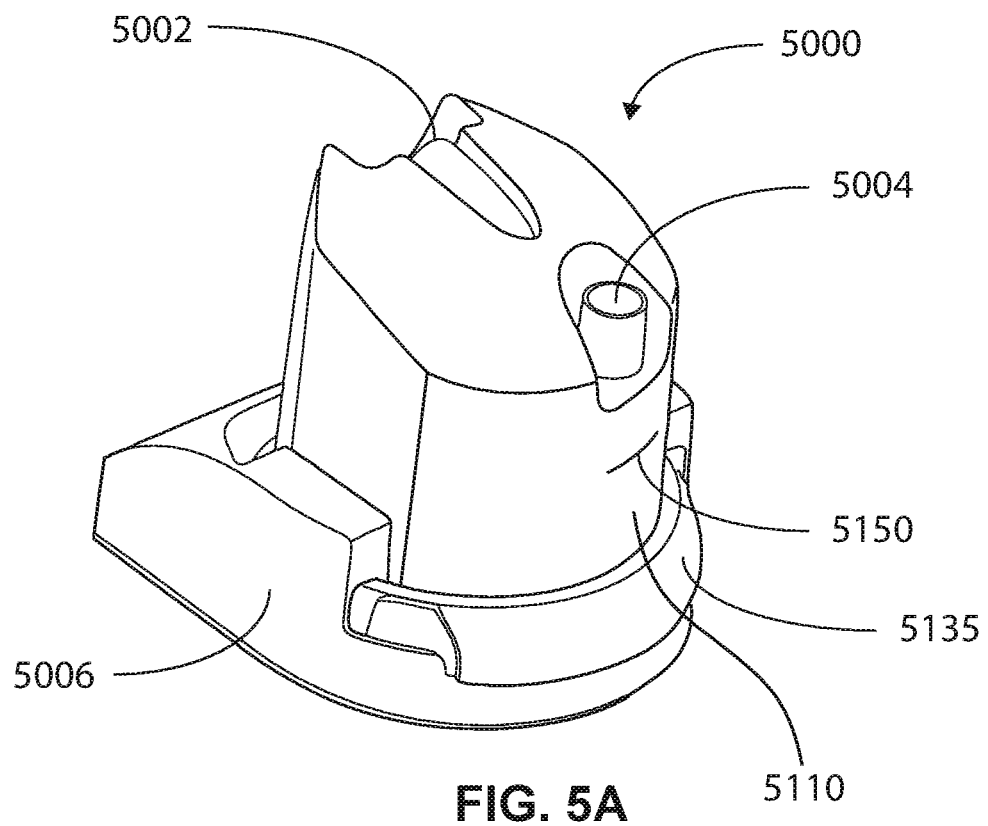

FIG. 5A shows an isometric view of a humidifier in accordance with one form of the present technology.

Figure 5B:
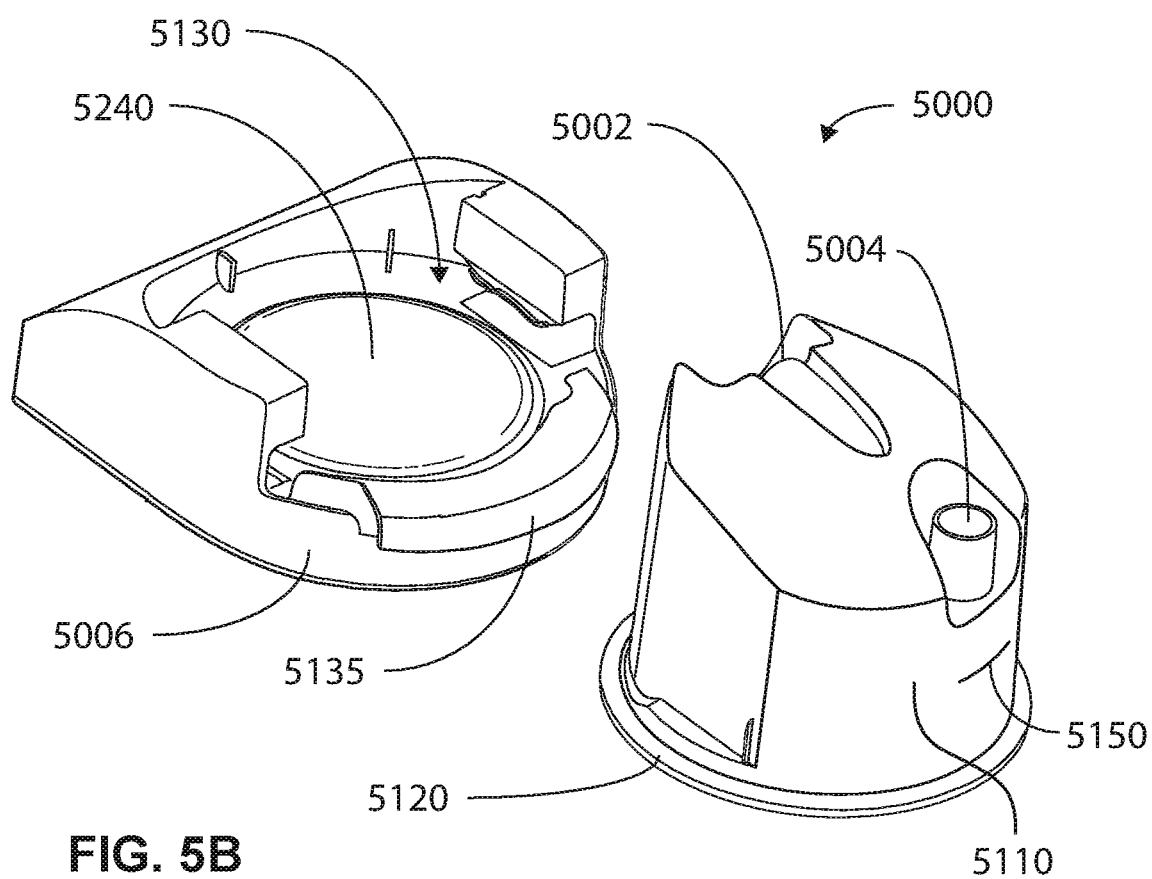

FIG. 5B shows an isometric view of a humidifier in accordance with one form of the present technology, showing a humidifier reservoir 5110 removed from the humidifier reservoir dock 5130.

Figure 5C:
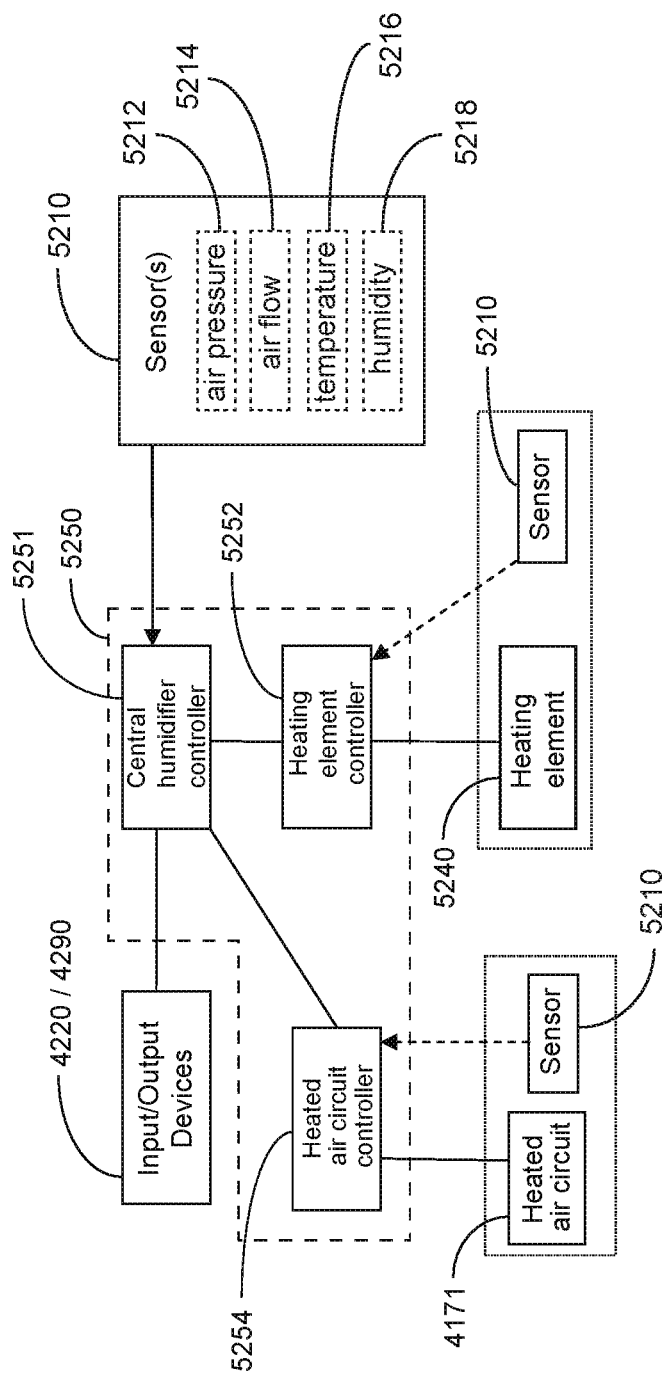

FIG. 5C shows a schematic of a humidifier in accordance with one form of the present technology.

4.6 Breathing Waveforms

Figure 6A:
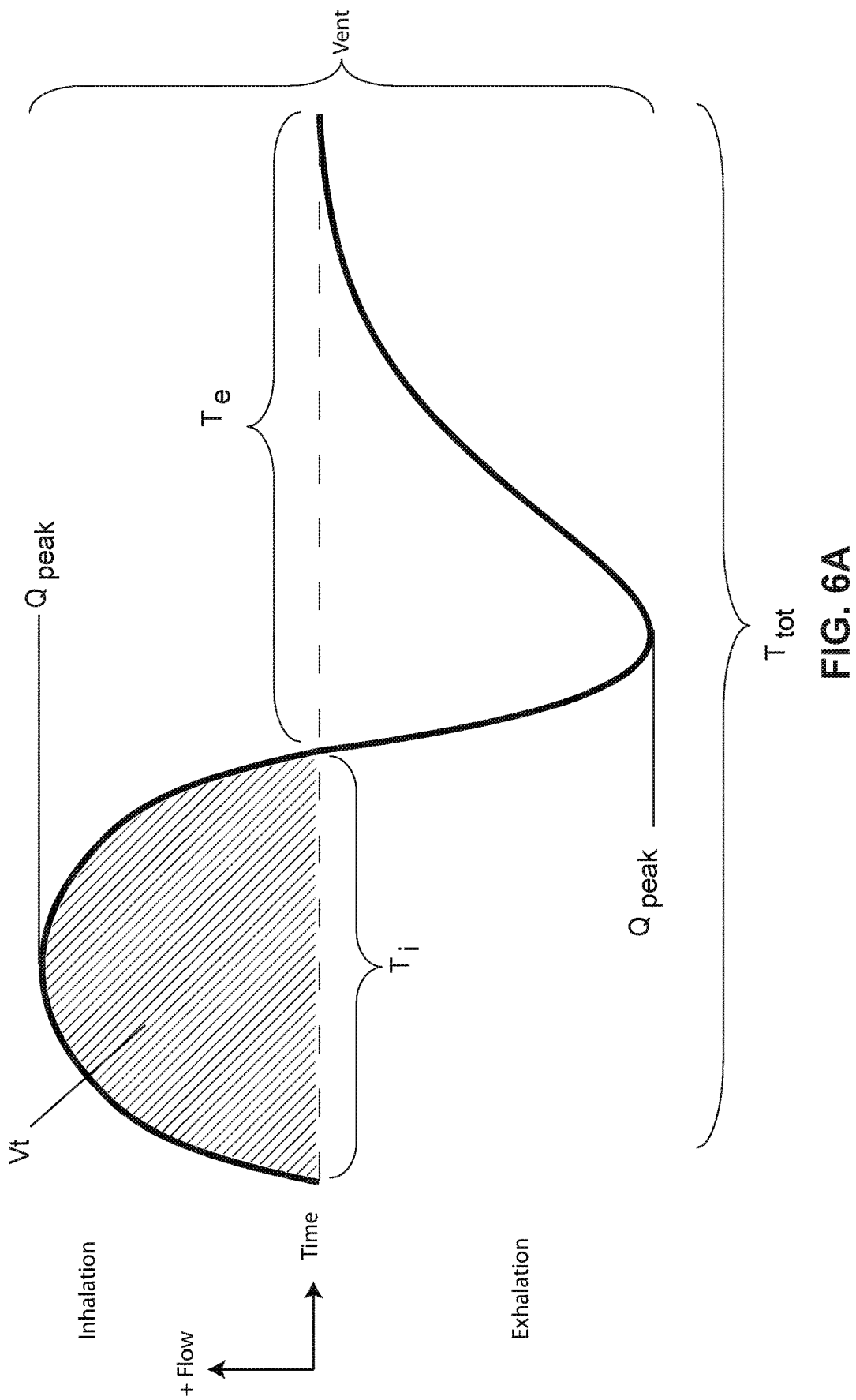

FIG. 6A shows a model typical breath waveform of a person while sleeping.

Figure 6B:
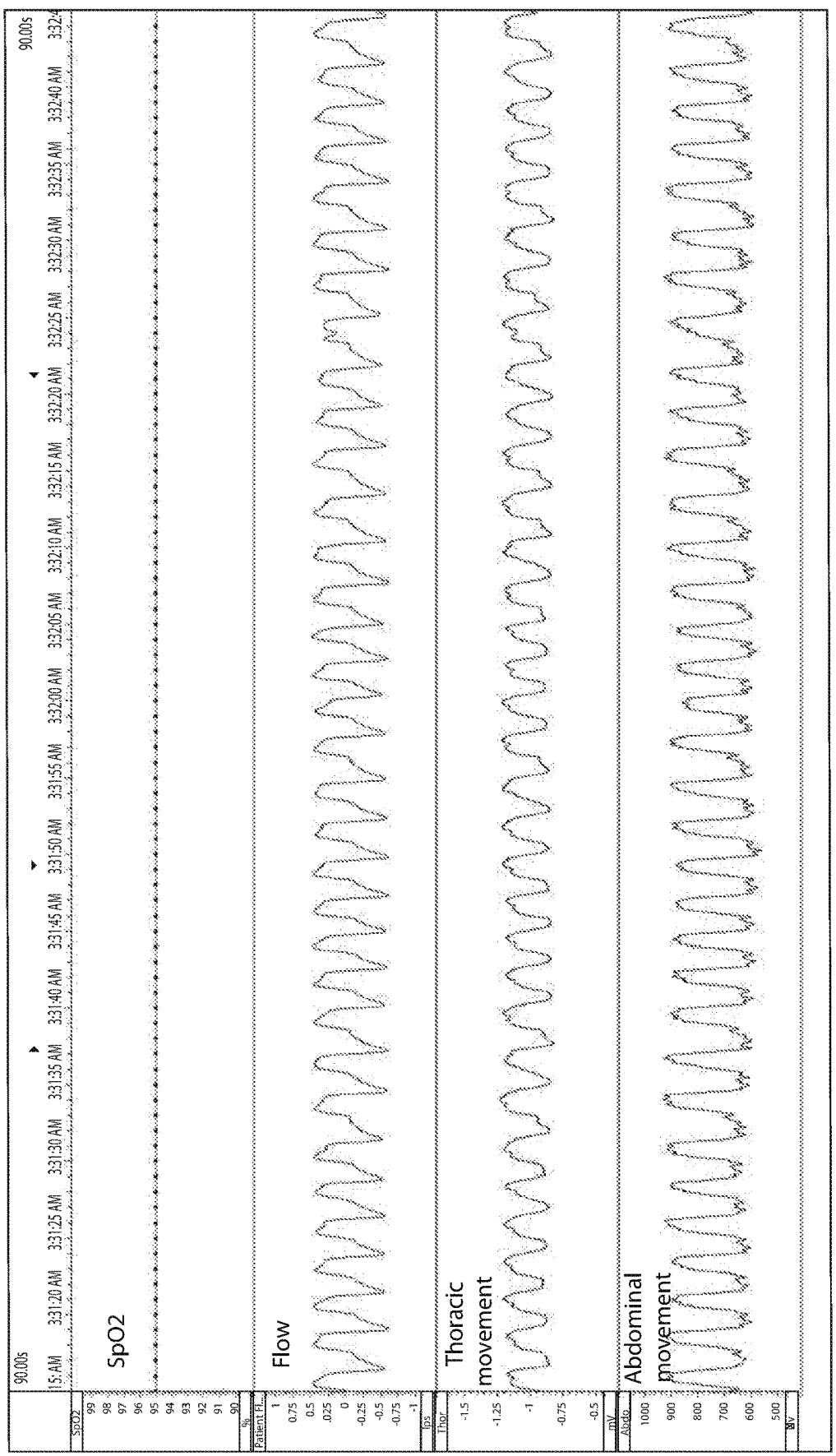

FIG. 6B shows selected polysomnography channels (pulse oximetry, flow rate, thoracic movement, and abdominal movement) of a patient during non-REM sleep breathing normally over a period of about ninety seconds.

4.7 Screening, Diagnosis and Monitoring Systems

Figure 7A:
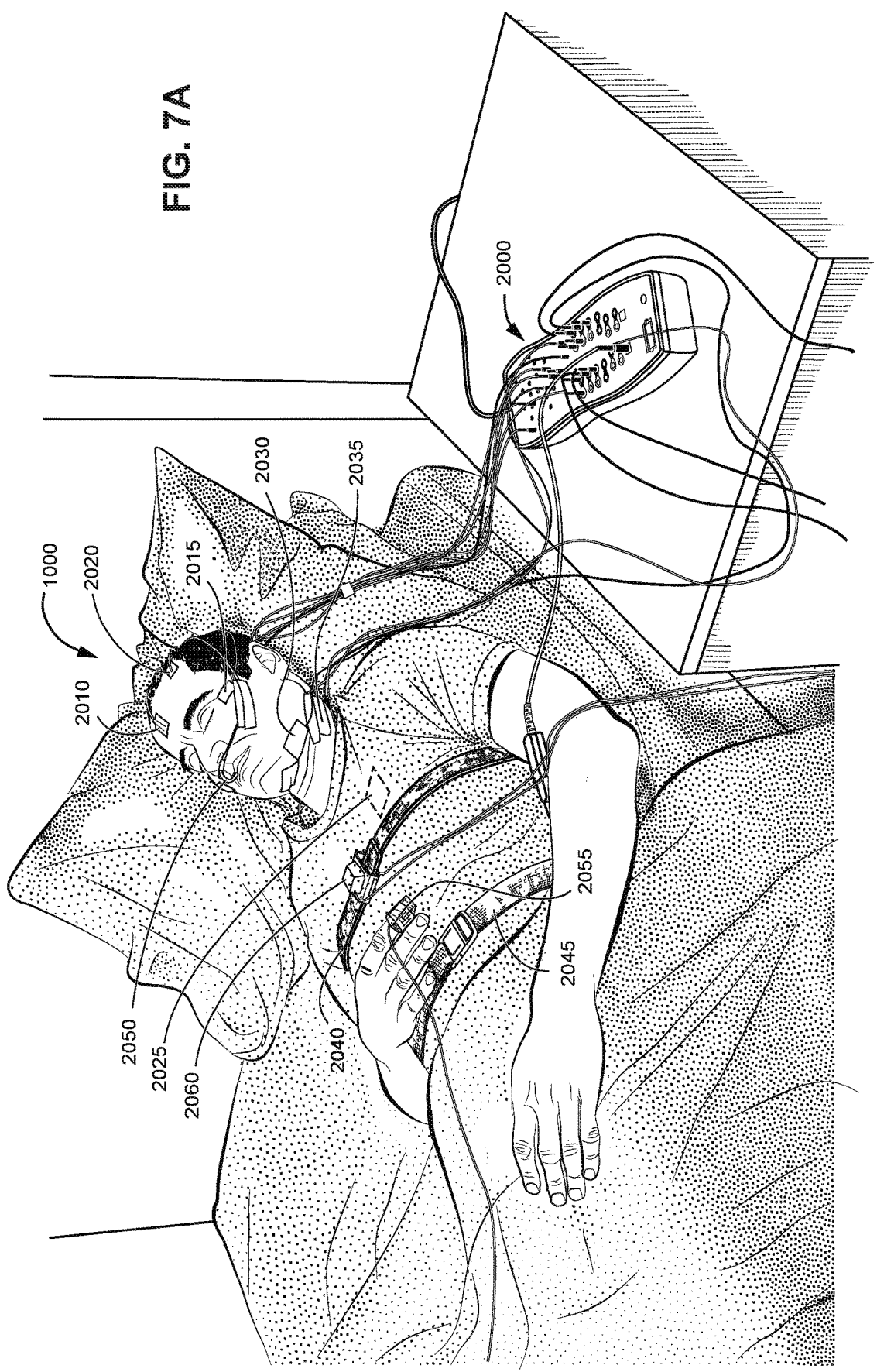

FIG. 7A shows a patient undergoing polysomnography (PSG). The patient is sleeping in a supine sleeping position.

Figure 7B:
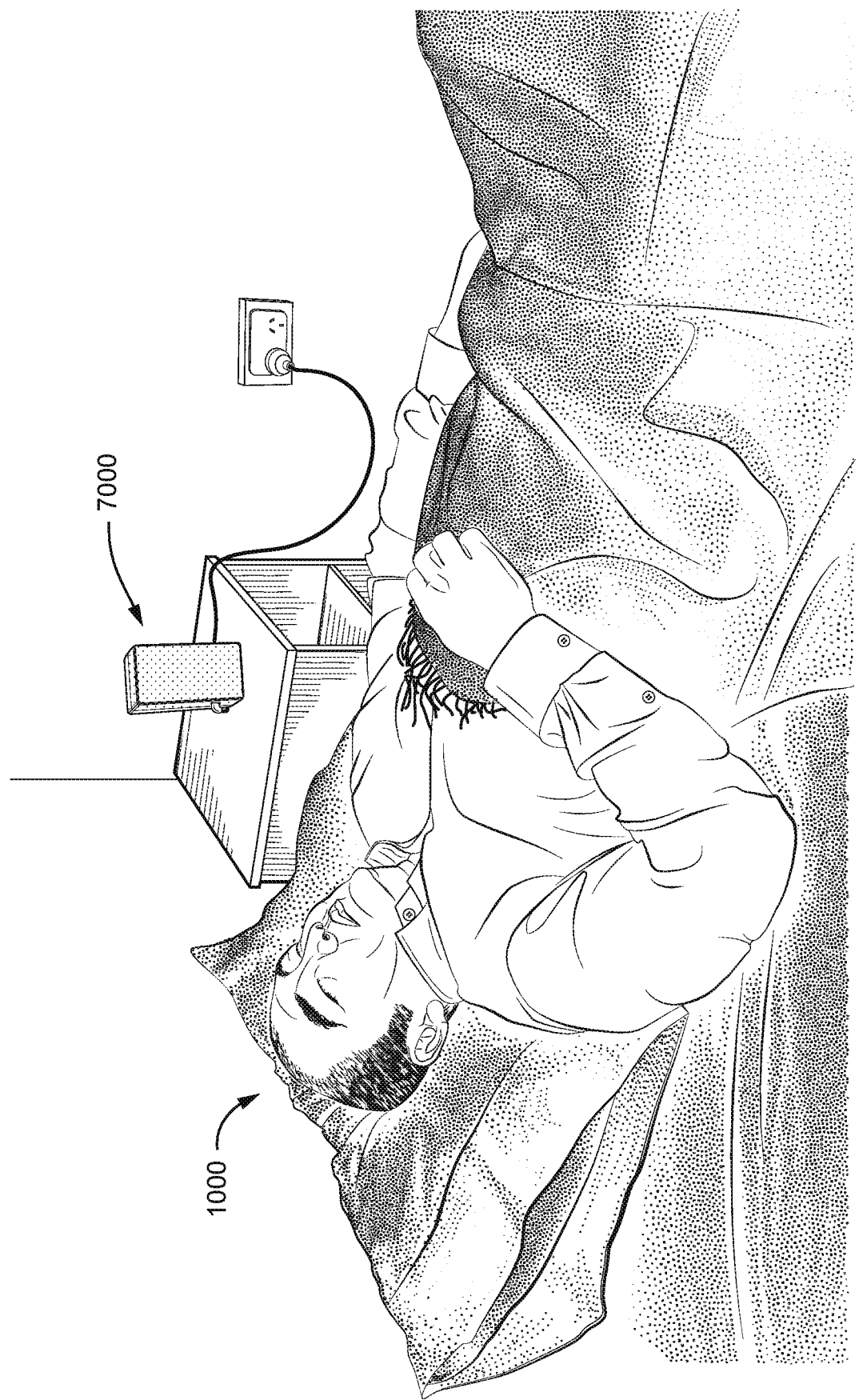

FIG. 7B shows a monitoring apparatus for monitoring the condition of a patient. The patient is sleeping in a supine sleeping position.

4.8 Data Transmission

Figure 8A:
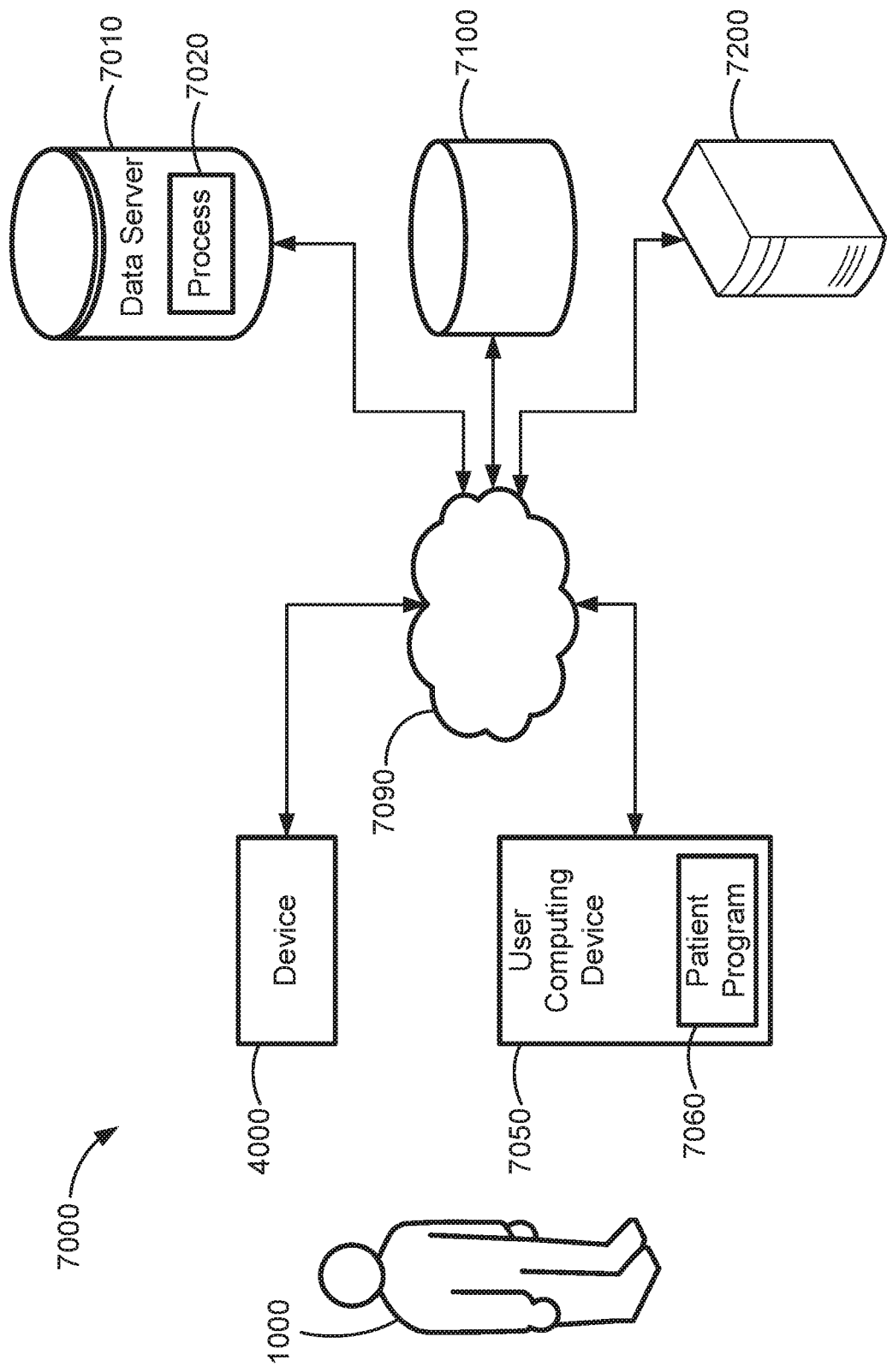

FIG. 8A is a block diagram of a system that receives usage data, and other data from a respiratory therapy device.

Figure 8B:
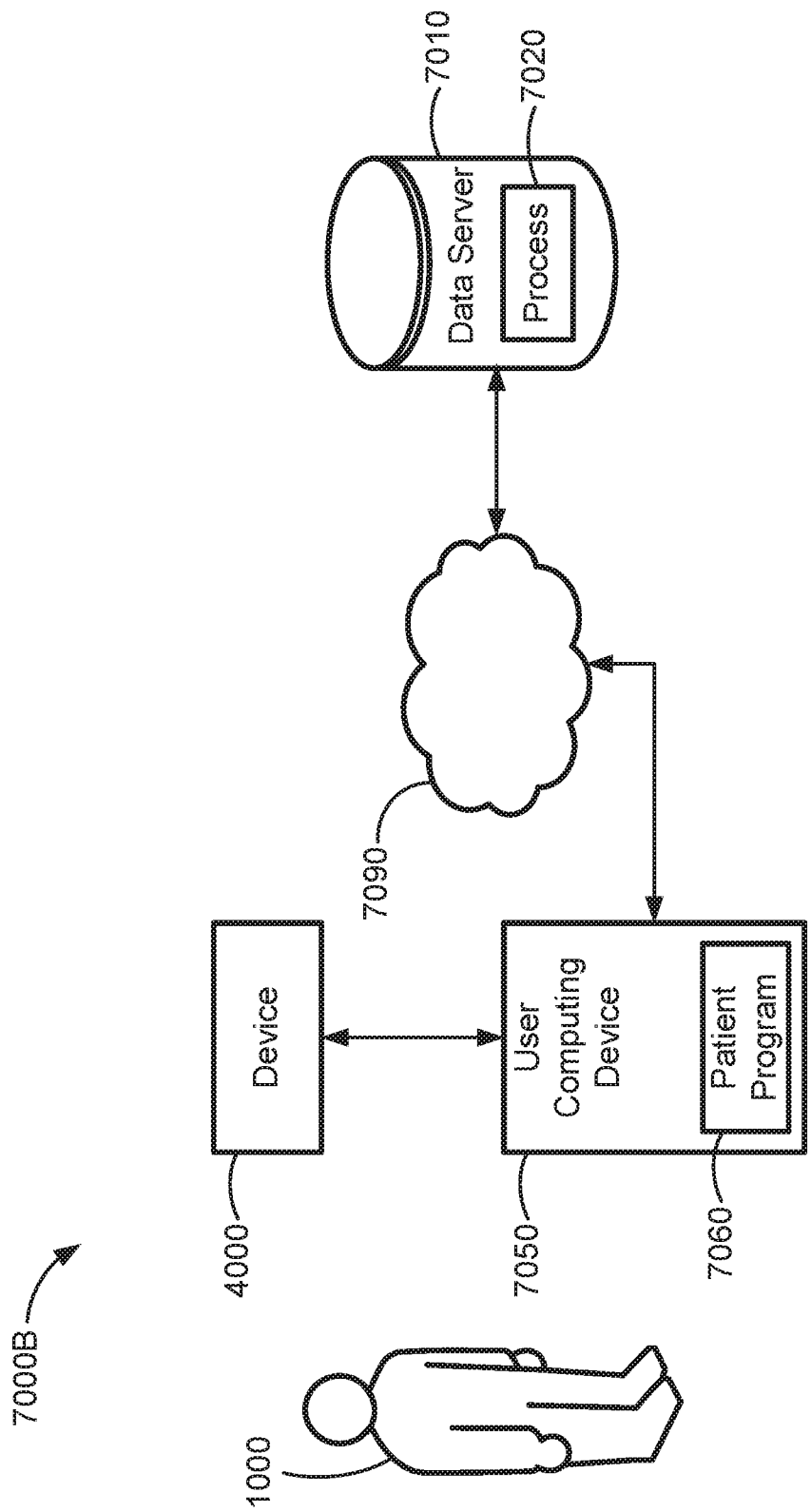

FIG. 8B is a block diagram of an alternate system that receives usage data, and other data from a respiratory therapy device.

4.9 Prediction of Reduction or Termination of Therapy

Figure 9:
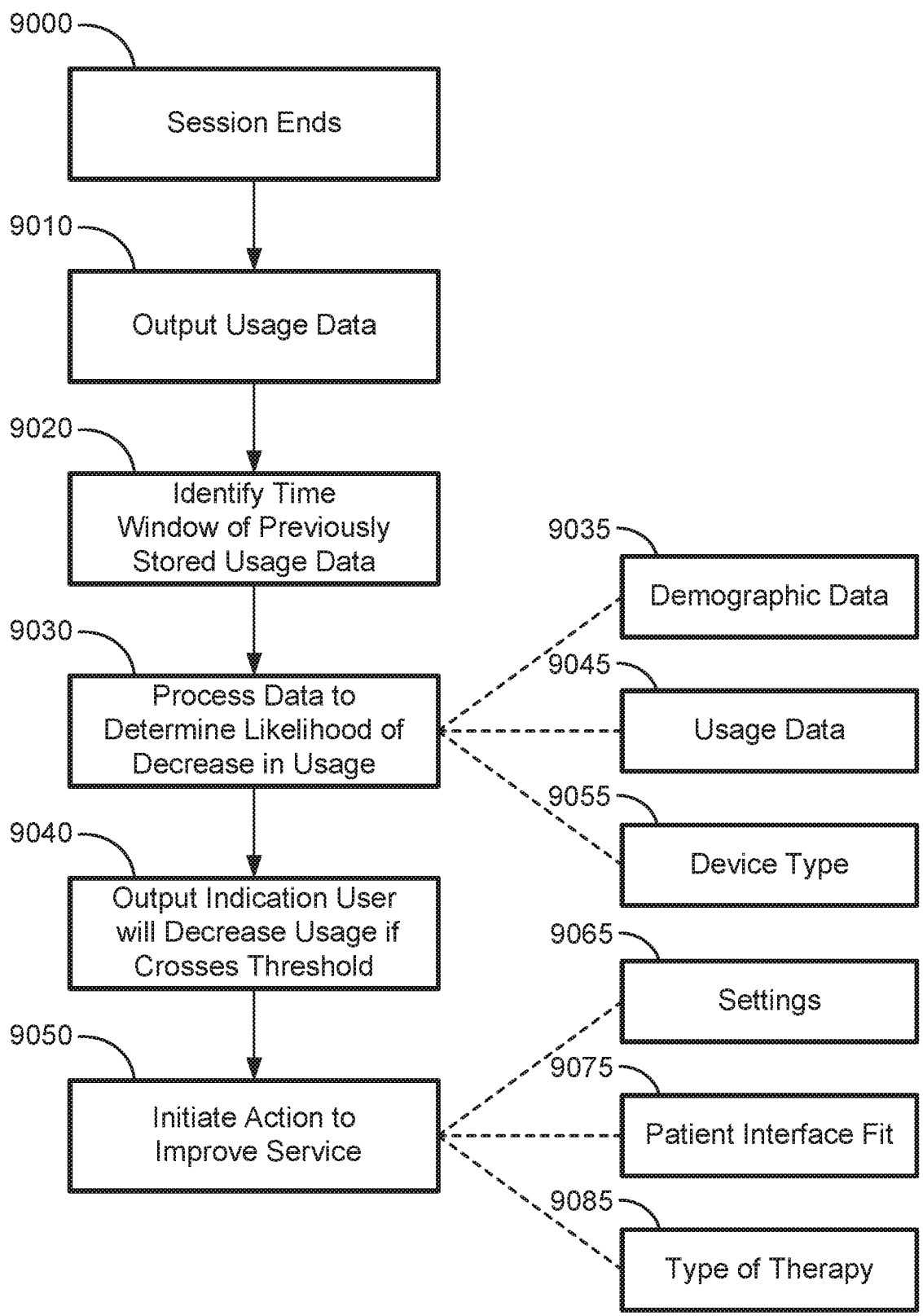

FIG. 9. shows a flow chart illustrating a method of predicting patient compliance based on usage data output from a respiratory therapy device.

Figure 10:
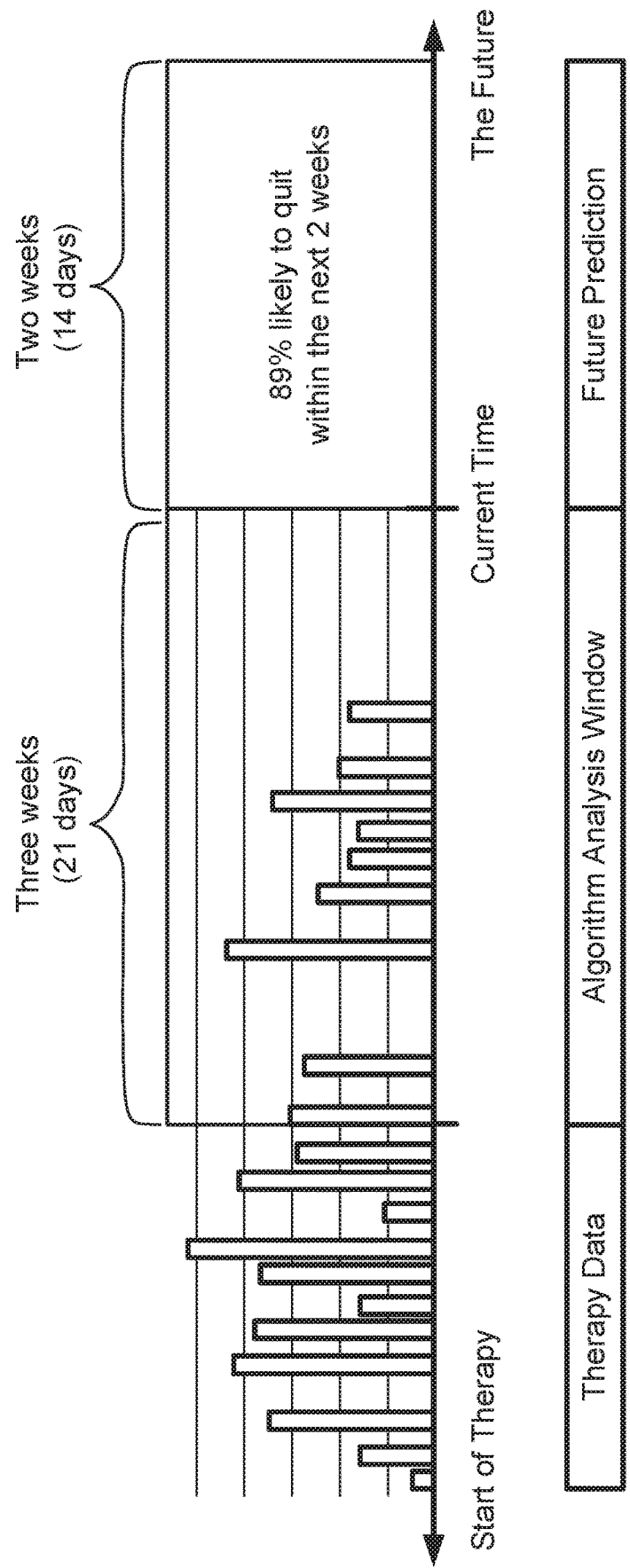

FIG. 10. shows a schematic diagram of an example of a time window of usage data considered in an algorithm applied with the disclosed technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000 or 3800.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

An unsealed patient interface 3800, in the form of a nasal cannula, includes nasal prongs 3810a, 3810b which can deliver air to respective nares of the patient 1000. Such nasal prongs do not generally form a seal with the inner or outer skin surface of the nares. The air to the nasal prongs may be delivered by one or more air supply lumens 3820a, 3820b that are coupled with the nasal cannula 3800. The lumens 3820a, 3820b lead from the nasal cannula 3800 lead to an RT device that generates the flow of air at high flow rates. The "vent" at the unsealed patient interface 3800, through which excess airflow escapes to ambient, is the passage between the end of the prongs 3810a and 3810b of the cannula 3800 via the patient's nares to atmosphere.

If a patient interface is unable to comfortably deliver a minimum level of positive pressure to the airways, the patient interface may be unsuitable for respiratory pressure therapy.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example, the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

5.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example, the system may comprise one form of positioning and stabilizing structure 3300 suitable for a large sized head, but not a small sized head, and another. suitable for a small sized head, but not a large sized head.

In certain forms of the present technology, a stabilizing structure 3300 contains sensors that are configured output data relating to the tensile force along a longitudinal axis of the straps or other related force, stress or mechanical values. In other examples, a stabilizing structure 3300 may include a pressure sensor on the side that senses pressure of the straps against a patient's head.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

In one form of the present technology, the vent 3400 may include an acoustical sensor to determine whether vent noise is emanating from the vent 3400. For instance, the acoustical sensor on the vent 3400 may be compared to the noise output from a remote sensor or a sensor on another component of the RPT device 4000 to determine noise associated with the vent 3400 as opposed to other components of the RPT device 4000.

5.3.5 Forehead Support

In one form, the patient interface 3000 includes a forehead support 3700.

5.3.6 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

5.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10 cmH$_2$O, or at least 20 cmH$_2$O.

5.4.1 RPT Device Mechanical & Pneumatic Components

An RPT device may comprise one or more of the following components in an integral unit. In an alternative form, one or more of the following components may be located as respective separate units.

5.4.1.1 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure, acoustical properties, or a temperature at that point in the pneumatic path.

In one form of the present technology, one or more transducers 4270 may be located proximate to the patient interface 3000 or 3800, including one or more acoustical sensors.

In one form, a signal from a transducer 4270 may be filtered, such as by low-pass, high-pass or band-pass filtering.

5.4.1.1.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate from the flow rate sensor 4274 is received by the central controller 4230.

5.4.1.1.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor 4272 is received by the central controller 4230.

5.4.1.1.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.2 RPT Device Electrical Components

5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device 4000 may include a clock 4232 that is connected to the central controller 4230.

5.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.4.2.8 Data Communication Systems

In one form of the present technology, a data communication interface 4280 is provided, and is connected to the central controller 4230 depending the system. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

In certain forms of the present technology, the central controller 4230 will record usage data 9045 in the memory 4260, which may include output from the therapy device controller 4240. The usage data 9045 may include several blocks or data divisions that include: (1) date and time stamps, (2) start and stop times of usage, (3) usage time for a session, (4) date and time of turning on and off RPT device 4000, and (5) therapy or other settings and sensor data, including readings from sensors 4270 including flow 4274, pressure 4272, and speed 4276.

In certain forms of the present technology, the usage data 9045 will be stored in the local memory 4260. The usage data 9045 may also be sent through the data communication interface 4280 to the remote external device 4286 through the network, or the local external device 4288.

In some examples, the central controller 4230 will send the usage data 9085 through the data communication interface 4280 an hour, two hours, three hours, or other suitable time frame after a therapy session has ended. In other examples, usage data 9045 will be sent on a weekly basis. In some examples, if no usage session has started on a particular day, the controller 4230 may send the usage data 9045 over the data communication interface 4280 by 1:00 a.m. or other suitable time the following day, or the end of the week. This usage data 9045 would indicate that a certain day or time period included a non-usage day. In some instances, the usage data 9045 may distinguish between: (1) turning on and not using a device (e.g. the RPT device 4000 and not turning on the device or system at all. In some examples, the RPT device 4000 or other device or system will not send the usage data 9045 until it is turned back on and will determine the amount of non-usage days since the last session identified and stored in the memory 4260 by the controller 4230.

The data sent over data communication interface 4280 may be raw data, or may be pre-processed data to save on bandwidth, especially in areas of poor cellular signal or other remote external communication network 4282 bandwidth. For instance, the usage data 9045 may be pre-processed to output relevant features for a usage reduction or termination prediction. This may include non-usage days, average usage (e.g. hours), and standard deviation of usage. Then, the relevant features may be processed by algorithms 4300 on a remote external device 4286 or server.

In certain forms of the present technology, full usage prediction algorithms may reside in the local memory 4260 and the controller 4230 may process the usage data 9045 to determine the likelihood a patient 1000 will quit or reduce usage on the device itself. In those cases, the controller 4230 may send a signal to send an output to the display 4294, and/or send data to a local or remote external device, for instance if the percentage likelihood crosses a threshold.

5.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

In some examples, the display may include touchscreen or a remote interface such as a smartphone that receives user or patient 1000 input.

5.4.3 Algorithms

As mentioned above, in some forms of the present technology, the central controller 4230 or other processors may be configured to implement one or more algorithms expressed as computer programs stored in a non-transitory computer readable storage medium, such as memory 4260. The algorithms are generally grouped into groups referred to as modules. These algorithms may include feature detection algorithms and machine learning algorithms for predicting decreasing or termination of therapy.

5.4.3.1 Pre-Processing Module

A pre-processing module 4310 in accordance with one form of the present technology receives as an input a signal from a transducer 4270, for example a flow rate sensor 4274 or pressure sensor 4272, and performs one or more process steps to calculate one or more output values that will be used as an input to another module, for example a therapy engine module 4320.

In one form of the present technology, the output values include the interface pressure Pm, the respiratory flow rate Qr, and the leak flow rate Ql.

In various forms of the present technology, the pre-processing module 4310 comprises one or more of the following algorithms: interface pressure estimation 4312, vent flow rate estimation 4314, leak flow rate estimation 4316, and respiratory flow rate estimation 4318.

5.4.3.1.1 Interface Pressure Estimation

In one form of the present technology, an interface pressure estimation algorithm 4312 receives as inputs a signal from the pressure sensor 4272 indicative of the pressure in the pneumatic path proximal to an outlet of the pneumatic block (the device pressure Pd) and a signal from the flow rate sensor 4274 representative of the flow rate of the airflow leaving the RPT device 4000 (the device flow rate Qd). The device flow rate Qd, absent any supplementary gas 4180, may be used as the total flow rate Qt. The interface pressure algorithm 4312 estimates the pressure drop $\Delta P$ through the air circuit 4170. The dependence of the pressure drop $\Delta P$ on the total flow rate Qt may be modelled for the particular air circuit 4170 by a pressure drop characteristic $\Delta P(Q)$. The interface pressure estimation algorithm, 4312 then provides as an output an estimated pressure, Pm, in the patient interface 3000 or 3800. The pressure, Pm, in the patient interface 3000 or 3800 may be estimated as the device pressure Pd minus the air circuit pressure drop $\Delta P$.

5.4.3.1.2 Vent Flow Rate Estimation

In one form of the present technology, a vent flow rate estimation algorithm 4314 receives as an input an estimated pressure, Pm, in the patient interface 3000 or 3800 from the interface pressure estimation algorithm 4312 and estimates a vent flow rate of air, Qv, from a vent 3400 in a patient interface 3000 or 3800. The dependence of the vent flow rate Qv on the interface pressure Pm for the particular vent 3400 in use may be modelled by a vent characteristic Qv(Pm).

5.4.3.1.3 Leak Flow Rate Estimation

In one form of the present technology, a leak flow rate estimation algorithm 4316 receives as an input a total flow rate, Qt, and a vent flow rate Qv, and provides as an output an estimate of the leak flow rate Ql. In one form, the leak flow rate estimation algorithm estimates the leak flow rate Ql by calculating an average of the difference between total flow rate Qt and vent flow rate Qv over a period sufficiently long to include several breathing cycles, e.g. about 10 seconds.

In one form, the leak flow rate estimation algorithm 4316 receives as an input a total flow rate Qt, a vent flow rate Qv, and an estimated pressure, Pm, in the patient interface 3000 or 3800, and provides as an output a leak flow rate Ql, by calculating a leak conductance, and determining a leak flow rate Ql to be a function of leak conductance and pressure, Pm. Leak conductance is calculated as the quotient of low pass filtered non-vent flow rate equal to the difference between total flow rate Qt and vent flow rate Qv, and low pass filtered square root of pressure Pm, where the low pass filter time constant has a value sufficiently long to include several breathing cycles, e.g. about 10 seconds. The leak flow rate Ql may be estimated as the product of leak conductance and a function of pressure, Pm.

5.4.3.1.4 Respiratory Flow Rate Estimation

In one form of the present technology, a respiratory flow rate estimation algorithm 4318 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

5.4.3.2 Therapy Engine Module

In one form of the present technology, a therapy engine module 4320 receives as inputs one or more of a pressure, Pm, in a patient interface 3000 or 3800, and a respiratory flow rate of air to a patient, Qr, and provides as an output one or more therapy parameters.

In one form of the present technology, a therapy parameter is a treatment pressure Pt.

In one form of the present technology, therapy parameters are one or more of an amplitude of a pressure variation, a base pressure, and a target ventilation.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, target ventilation determination 4328, and therapy parameter determination 4329.

5.4.3.2.1 Phase Determination

In one form of the present technology, the RPT device 4000 does not determine phase.

In one form of the present technology, a phase determination algorithm 4321 receives as an input a signal indicative of respiratory flow rate, Qr, and provides as an output a phase Φ of a current breathing cycle of a patient 1000.

In some forms, known as discrete phase determination, the phase output Φ is a discrete variable. One implementation of discrete phase determination provides a bi-valued phase output Φ with values of either inhalation or exhalation, for example represented as values of 0 and 0.5 revolutions respectively, upon detecting the start of spontaneous inhalation and exhalation respectively. RPT devices 4000 that "trigger" and "cycle" effectively perform discrete phase determination, since the trigger and cycle points are the instants at which the phase changes from exhalation to inhalation and from inhalation to exhalation, respectively. In one implementation of bi-valued phase determination, the phase output Φ is determined to have a discrete value of 0 (thereby "triggering" the RPT device 4000) when the respiratory flow rate Qr has a value that exceeds a positive threshold, and a discrete value of 0.5 revolutions (thereby "cycling" the RPT device 4000) when a respiratory flow rate Qr has a value that is more negative than a negative threshold. The inhalation time Ti and the exhalation time Te may be estimated as typical values over many respiratory cycles of the time spent with phase Φ equal to 0 (indicating inspiration) and 0.5 (indicating expiration) respectively.

Another implementation of discrete phase determination provides a tri-valued phase output Φ with a value of one of inhalation, mid-inspiratory pause, and exhalation.

In other forms, known as continuous phase determination, the phase output Φ is a continuous variable, for example varying from 0 to 1 revolutions, or 0 to 2π radians. RPT devices 4000 that perform continuous phase determination may trigger and cycle when the continuous phase reaches 0 and 0.5 revolutions, respectively. In one implementation of continuous phase determination, a continuous value of phase Φ is determined using a fuzzy logic analysis of the respiratory flow rate Qr. A continuous value of phase determined in this implementation is often referred to as "fuzzy phase". In one implementation of a fuzzy phase determination algorithm 4321, the following rules are applied to the respiratory flow rate Qr:

1. If the respiratory flow rate is zero and increasing fast then the phase is 0 revolutions.
2. If the respiratory flow rate is large positive and steady then the phase is 0.25 revolutions.
3. If the respiratory flow rate is zero and falling fast, then the phase is 0.5 revolutions.
4. If the respiratory flow rate is large negative and steady then the phase is 0.75 revolutions.
5. If the respiratory flow rate is zero and steady and the 5-second low-pass filtered absolute value of the respiratory flow rate is large then the phase is 0.9 revolutions.
6. If the respiratory flow rate is positive and the phase is expiratory, then the phase is 0 revolutions.
7. If the respiratory flow rate is negative and the phase is inspiratory, then the phase is 0.5 revolutions.
8. If the 5-second low-pass filtered absolute value of the respiratory flow rate is large, the phase is increasing at a steady rate equal to the patient's breathing rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, are then combined by some function such as taking the centroid. In such a combination, the rules may be equally weighted, or differently weighted.

In another implementation of continuous phase determination, the phase Φ is first discretely estimated from the respiratory flow rate Qr as described above, as are the inhalation time Ti and the exhalation time Te. The continuous phase Φ at any instant may be determined as the half the proportion of the inhalation time Ti that has elapsed since the previous trigger instant, or 0.5 revolutions plus half the proportion of the exhalation time Te that has elapsed since the previous cycle instant (whichever instant was more recent).

5.4.3.2.2 Waveform Determination

In one form of the present technology, the therapy parameter determination algorithm 4329 provides an approximately constant treatment pressure throughout a respiratory cycle of a patient.

In other forms of the present technology, the therapy control module 4330 controls the pressure generator 4140 to provide a treatment pressure Pt that varies as a function of phase Φ of a respiratory cycle of a patient according to a waveform template Π(Φ).

In one form of the present technology, a waveform determination algorithm 4322 provides a waveform template Π(Φ) with values in the range [0, 1] on the domain of phase values Φ provided by the phase determination algorithm 4321 to be used by the therapy parameter determination algorithm 4329.

In one form, suitable for either discrete or continuously-valued phase, the waveform template Π(Φ) is a square-wave template, having a value of 1 for values of phase up to and including 0.5 revolutions, and a value of 0 for values of phase above 0.5 revolutions. In one form, suitable for continuously-valued phase, the waveform template Π(Φ) comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions. In one form, suitable for continuously-valued phase, the waveform template Π(Φ) is based on a square wave, but with a smooth rise from 0 to 1 for values of phase up to a "rise time" that is less than 0.5 revolutions, and a smooth fall from 1 to 0 for values of phase within a "fall time" after 0.5 revolutions, with a "fall time" that is less than 0.5 revolutions.

In some forms of the present technology, the waveform determination algorithm 4322 selects a waveform template Π(Φ) from a library of waveform templates, dependent on a setting of the RPT device. Each waveform template Π(Φ) in the library may be provided as a lookup table of values Π against phase values Φ. In other forms, the waveform determination algorithm 4322 computes a waveform template Π(Φ) "on the fly" using a predetermined functional form, possibly parametrised by one or more parameters (e.g. time constant of an exponentially curved portion). The parameters of the functional form may be predetermined or dependent on a current state of the patient 1000.

In some forms of the present technology, suitable for discrete bi-valued phase of either inhalation (Φ=0 revolutions) or exhalation (Φ=0.5 revolutions), the waveform determination algorithm 4322 computes a waveform template Π "on the fly" as a function of both discrete phase Φ and time t measured since the most recent trigger instant. In one such form, the waveform determination algorithm 4322 computes the waveform template Π(Φ, t) in two portions (inspiratory and expiratory) as follows:

$$\prod(\Phi, t) = \begin{cases} \prod_i(t), & \Phi = 0 \\ \prod_e(t - T_i), & \Phi = 0.5 \end{cases}$$

where $\Pi_I(t)$ and $\Pi_e(t)$ are inspiratory and expiratory portions of the waveform template $\Pi(\Phi, t)$. In one such form, the inspiratory portion $\Pi_I(t)$ of the waveform template is a smooth rise from 0 to 1 parametrised by a rise time, and the expiratory portion $\Pi_e(t)$ of the waveform template is a smooth fall from 1 to 0 parametrised by a fall time.

5.4.3.2.3 Ventilation Determination

In one form of the present technology, a ventilation determination algorithm 4323 receives an input a respiratory flow rate Qr, and determines a measure indicative of current patient ventilation, Vent.

In some implementations, the ventilation determination algorithm 4323 determines a measure of ventilation Vent that is an estimate of actual patient ventilation. One such implementation is to take half the absolute value of respiratory flow rate, Qr, optionally filtered by low-pass filter such as a second order Bessel low-pass filter with a corner frequency of 0.11 Hz.

In other implementations, the ventilation determination algorithm 4323 determines a measure of ventilation Vent that is broadly proportional to actual patient ventilation. One such implementation estimates peak respiratory flow rate Qpeak over the inspiratory portion of the cycle. This and many other procedures involving sampling the respiratory flow rate Qr produce measures which are broadly proportional to ventilation, provided the flow rate waveform shape does not vary very much (here, the shape of two breaths is taken to be similar when the flow rate waveforms of the breaths normalised in time and amplitude are similar). Some simple examples include the median positive respiratory flow rate, the median of the absolute value of respiratory flow rate, and the standard deviation of flow rate. Arbitrary linear combinations of arbitrary order statistics of the absolute value of respiratory flow rate using positive coefficients, and even some using both positive and negative coefficients, are approximately proportional to ventilation. Another example is the mean of the respiratory flow rate in the middle K proportion (by time) of the inspiratory portion, where 0<K<1. There is an arbitrarily large number of measures that are exactly proportional to ventilation if the flow rate shape is constant.

5.4.3.2.4 Determination of Inspiratory Flow Limitation

In one form of the present technology, the central controller 4230 executes an inspiratory flow limitation determination algorithm 4324 for the determination of the extent of inspiratory flow limitation.

In one form, the inspiratory flow limitation determination algorithm 4324 receives as an input a respiratory flow rate signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow rate-time curve for each breath. The curve described by the points is then scaled by a scalar to have unity length (duration/period) and unity area to remove the effects of changing breathing rate and depth. The scaled breaths are then compared in a comparator with a pre-stored template representing a normal unobstructed breath, similar to the inspiratory portion of the breath shown in FIG. 6A. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by the central controller 4230 for the preceding several inspiratory events. This is repeated over the same inspiratory events for the second such point, and so on. Thus, for example, sixty five scaled data points are generated by the central controller 4230, and represent a moving average of the preceding several inspiratory events, e.g., three events. The moving average of continuously updated values of the (e.g., sixty five) points are hereinafter called the "scaled flow rate", designated as Qs(t). Alternatively, a single inspiratory event can be utilised rather than a moving average.

From the scaled flow rate, two shape factors relating to the determination of partial obstruction may be calculated.

Shape factor 1 is the ratio of the mean of the middle (e.g. thirty-two) scaled flow rate points to the mean overall (e.g. sixty-five) scaled flow rate points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical patient.

Shape factor 2 is calculated as the RMS deviation from unit scaled flow rate, taken over the middle (e.g. thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can be other than those described.

5.4.3.2.5 Determination of Apneas and Hypopneas

In one form of the present technology, the central controller 4230 executes an apnea/hypopnea determination algorithm 4325 for the determination of the presence of apneas and/or hypopneas.

In one form, the apnea/hypopnea determination algorithm 4325 receives as an input a respiratory flow rate signal Qr and provides as an output a flag that indicates that an apnea or a hypopnea has been detected.

In one form, an apnea will be said to have been detected when a function of respiratory flow rate Qr falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In one form, a hypopnea will be said to have been detected when a function of respiratory flow rate Qr falls below a second flow rate threshold for a predetermined period of time. The function may determine a peak flow, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

5.4.3.2.6 Determination of Snore

In one form of the present technology, the central controller 4230 executes one or more snore determination algorithms 4326 for the determination of the extent of snore.

In one form, the snore determination algorithm 4326 receives as an input a respiratory flow rate signal Qr and provides as an output a metric of the extent to which snoring is present.

The snore determination algorithm 4326 may comprise the step of determining the intensity of the flow rate signal in the range of 30-300 Hz. Further, the snore determination algorithm 4326 may comprise a step of filtering the respiratory flow rate signal Qr to reduce background noise, e.g., the sound of airflow in the system from the blower.

5.4.3.2.7 Determination of Airway Patency

In one form of the present technology, the central controller 4230 executes one or more airway patency determination algorithms 4327 for the determination of the extent of airway patency.

In one form, the airway patency determination algorithm 4327 receives as an input a respiratory flow rate signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 cmH$_2$O.

In one form, airway patency determination algorithm 4327 receives as an input a respiratory flow rate signal Qr, and determines the presence or absence of a cardiogenic signal. The absence of a cardiogenic signal is taken to be an indication of a closed airway.

5.4.3.2.8 Determination of Target Ventilation

In one form of the present technology, the central controller 4230 takes as input the measure of current ventilation, Vent, and executes one or more target ventilation determination algorithms 4328 for the determination of a target value Vtgt for the measure of ventilation.

In some forms of the present technology, there is no target ventilation determination algorithm 4328, and the target value Vtgt is predetermined, for example by hard-coding during configuration of the RPT device 4000 or by manual entry through the input device 4220.

In other forms of the present technology, such as adaptive servo-ventilation (ASV), the target ventilation determination algorithm 4328 computes a target value Vtgt from a value Vtyp indicative of the typical recent ventilation of the patient.

In some forms of adaptive servo-ventilation, the target ventilation Vtgt is computed as a high proportion of, but less than, the typical recent ventilation Vtyp. The high proportion in such forms may be in the range (80%, 100%), or (85%, 95%), or (87%, 92%).

In other forms of adaptive servo-ventilation, the target ventilation Vtgt is computed as a slightly greater than unity multiple of the typical recent ventilation Vtyp.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4328, the recent history is of the order of several minutes, but in any case should be longer than the timescale of Cheyne-Stokes waxing and waning cycles. The target ventilation determination algorithm 4328 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

5.4.3.2.9 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320. This may include algorithms 4300 for changing therapy parameters if a patient 1000 is flagged for decreasing or terminating therapy.

In one form of the present technology, the therapy parameter is an instantaneous treatment pressure Pt. In one implementation of this form, the therapy parameter determination algorithm 4329 determines the treatment pressure Pt using the equation $$Pt = A\Pi(\Phi, t) + P_0 \tag{1}$$

where:

A is the amplitude, $\Pi(\Phi, t)$ is the waveform template value (in the range 0 to 1) at the current value $\Phi$ of phase and t of time, and $P_0$ is a base pressure.

If the waveform determination algorithm 4322 provides the waveform template $\Pi(\Phi, t)$ as a lookup table of values $\Pi$ indexed by phase $\Phi$, the therapy parameter determination algorithm 4329 applies equation (1) by locating the nearest lookup table entry to the current value $\Phi$ of phase returned by the phase determination algorithm 4321, or by interpolation between the two entries straddling the current value $\Phi$ of phase.

The values of the amplitude A and the base pressure $P_0$ may be set by the therapy parameter determination algorithm 4329 depending on the chosen respiratory pressure therapy mode in the manner described below.

5.4.3.3 Therapy Control Module

The therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose interface pressure Pm at the patient interface 3000 or 3800 is equal to the treatment pressure Pt.

5.4.3.4 Detection of Fault Conditions

In one form of the present technology, the central controller 4230 executes one or more methods 4340 for the detection of fault conditions. The fault conditions detected by the one or more methods 4340 may include at least one of the following:

Power failure (no power, or insufficient power)

Transducer fault detection

Failure to detect the presence of a component

Operating parameters outside recommended ranges (e.g. pressure, flow rate, temperature, PaO$_2$)

Failure of a test alarm to generate a detectable alarm signal.

Upon detection of the fault condition, the corresponding algorithm 4340 signals the presence of the fault by one or more of the following:

Initiation of an audible, visual &/or kinetic (e.g. vibrating) alarm

Sending a message to an external device

Logging of the incident

5.5 Humidifier

5.5.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

FIG. 6B shows selected polysomnography channels (pulse oximetry, flow rate, thoracic movement, and abdominal movement) of a patient during non-REM sleep breathing normally over a period of about ninety seconds, with about 34 breaths, being treated with automatic PAP therapy, and the interface pressure being about 11 cmH$_2$O. The top channel shows pulse oximetry (oxygen saturation or SpO$_2$), the scale having a range of saturation from 90 to 99% in the vertical direction. The patient maintained a saturation of about 95% throughout the period shown. The second channel shows quantitative respiratory airflow, and the scale ranges from −1 to +1 LPS in a vertical direction, and with inspiration positive. Thoracic and abdominal movement are shown in the third and fourth channels.

5.7 Screening, Diagnosis, Monitoring Systems

5.7.1 Polysomnography

FIG. 7A shows a patient 1000 undergoing polysomnography (PSG). A PSG system comprises a headbox 2000 which receives and records signals from the following sensors: an EOG electrode 2015; an EEG electrode 2020; an ECG electrode 2025; a submental EMG electrode 2030; a snore sensor 2035; a respiratory inductance plethysmogram (respiratory effort sensor) 2040 on a chest band; a respiratory inductance plethysmogram (respiratory effort sensor) 2045 on an abdominal band; an oro-nasal cannula 2050 with oral thermistor; a photoplethysmograph (pulse oximeter) 2055; and a body position sensor 2060. The electrical signals are referred to a ground electrode (ISOG) 2010 positioned in the centre of the forehead.

5.7.2 Non-Obtrusive Monitoring System

One example of a monitoring apparatus 7100 for monitoring the respiration of a sleeping patient 1000 is illustrated in FIG. 7B. The monitoring apparatus 7100 contains a contactless motion sensor generally directed toward the patient 1000. The motion sensor is configured to generate one or more signals representing bodily movement of the patient 1000, from which may be obtained a signal representing respiratory movement of the patient. In other examples, the system may include environmental and other acoustical sensors to sense ambient, vent and patient 1000 noise.

5.7.3 Respiratory Polygraphy

Respiratory polygraphy (RPG) is a term for a simplified form of PSG without the electrical signals (EOG, EEG, EMG), snore, or body position sensors. RPG comprises at least a thoracic movement signal from a respiratory inductance plethysmogram (movement sensor) on a chest band, e.g. the movement sensor 2040, a nasal pressure signal sensed via a nasal cannula, and an oxygen saturation signal from a pulse oximeter, e.g. the pulse oximeter 2055. The three RPG signals, or channels, are received by an RPG headbox, similar to the PSG headbox 2000.

In certain configurations, a nasal pressure signal is a satisfactory proxy for a nasal flow rate signal generated by a flow rate transducer in-line with a sealed nasal mask, in that the nasal pressure signal is comparable in shape to the nasal flow rate signal. The nasal flow rate in turn is equal to the respiratory flow rate if the patient's mouth is kept closed, i.e. in the absence of mouth leaks.

FIG. 7C is a block diagram illustrating a screening/diagnosis/monitoring device 7200 that may be used to implement an RPG headbox in an RPG screening/diagnosis/monitoring system. The screening/diagnosis/monitoring device 7200 receives the three RPG channels mentioned above (a signal indicative of thoracic movement, a signal indicative of nasal flow rate, and a signal indicative of oxygen saturation) at a data input interface 7260. The screening/diagnosis/monitoring device 7200 also contains a processor 7210 configured to carry out encoded instructions. The screening/diagnosis/monitoring device 7200 also contains a non-transitory computer readable memory/storage medium 7230.

Memory 7230 may be the screening/diagnosis/monitoring device 7200's internal memory, such as RAM, flash memory or ROM. In some implementations, memory 7230 may also be a removable or external memory linked to screening/diagnosis/monitoring device 7200, such as an SD card, server, USB flash drive or optical disc, for example. In other implementations, memory 7230 can be a combination of external and internal memory. Memory 7230 includes stored data 7240 and processor control instructions (code) 7250 adapted to configure the processor 7210 to perform certain tasks. Stored data 7240 can include RPG channel data received by data input interface 7260, and other data that is provided as a component part of an application. Processor control instructions 7250 can also be provided as a component part of an application program. The processor 7210 is configured to read the code 7250 from the memory 7230 and execute the encoded instructions. In particular, the code 7250 may contain instructions adapted to configure the processor 7210 to carry out methods of processing the RPG channel data provided by the interface 7260. One such method may be to store the RPG channel data as data 7240 in the memory 7230. Another such method may be to analyse the stored RPG data to extract features. The processor 7210 may store the results of such analysis as data 7240 in the memory 7230.

The screening/diagnosis/monitoring device 7200 may also contain a communication interface 7220. The code 7250 may contain instructions configured to allow the processor 7210 to communicate with an external computing device (not shown) via the communication interface 7220. The mode of communication may be wired or wireless. In one such implementation, the processor 7210 may transmit the stored RPG channel data from the data 7240 to the remote computing device. In such an implementation, the remote computing device may be configured to analyse the received RPG data to extract features. In another such implementation, the processor 7210 may transmit the analysis results from the data 7240 to the remote computing device.

Alternatively, if the memory 7230 is removable from the screening/diagnosis/monitoring device 7200, the remote computing device may be configured to be connected to the removable memory 7230. In such an implementation, the remote computing device may be configured to analyse the RPG data retrieved from the removable memory 7230 to extract the features.

5.8 Respiratory Therapy Modes

Various respiratory therapy modes may be implemented by the RPT device 4000.

5.8.1 CPAP Therapy

In some implementations of respiratory pressure therapy, the central controller 4230 sets the treatment pressure Pt according to the treatment pressure equation (1) as part of the therapy parameter determination algorithm 4329. In one such implementation, the amplitude A is identically zero, so the treatment pressure Pt (which represents a target value to be achieved by the interface pressure Pm at the current instant of time) is identically equal to the base pressure $P_0$ throughout the respiratory cycle. Such implementations are generally grouped under the heading of CPAP therapy. In such implementations, there is no need for the therapy engine module 4320 to determine phase Φ or the waveform template Π(Φ).

In CPAP therapy, the base pressure $P_0$ may be a constant value that is hard-coded or manually entered to the RPT device 4000. Alternatively, the central controller 4230 may repeatedly compute the base pressure $P_0$ as a function of indices or measures of sleep disordered breathing returned by the respective algorithms in the therapy engine module 4320, such as one or more of flow limitation, apnea, hypopnea, patency, and snore. This alternative is sometimes referred to as APAP therapy.

Figure 1A:
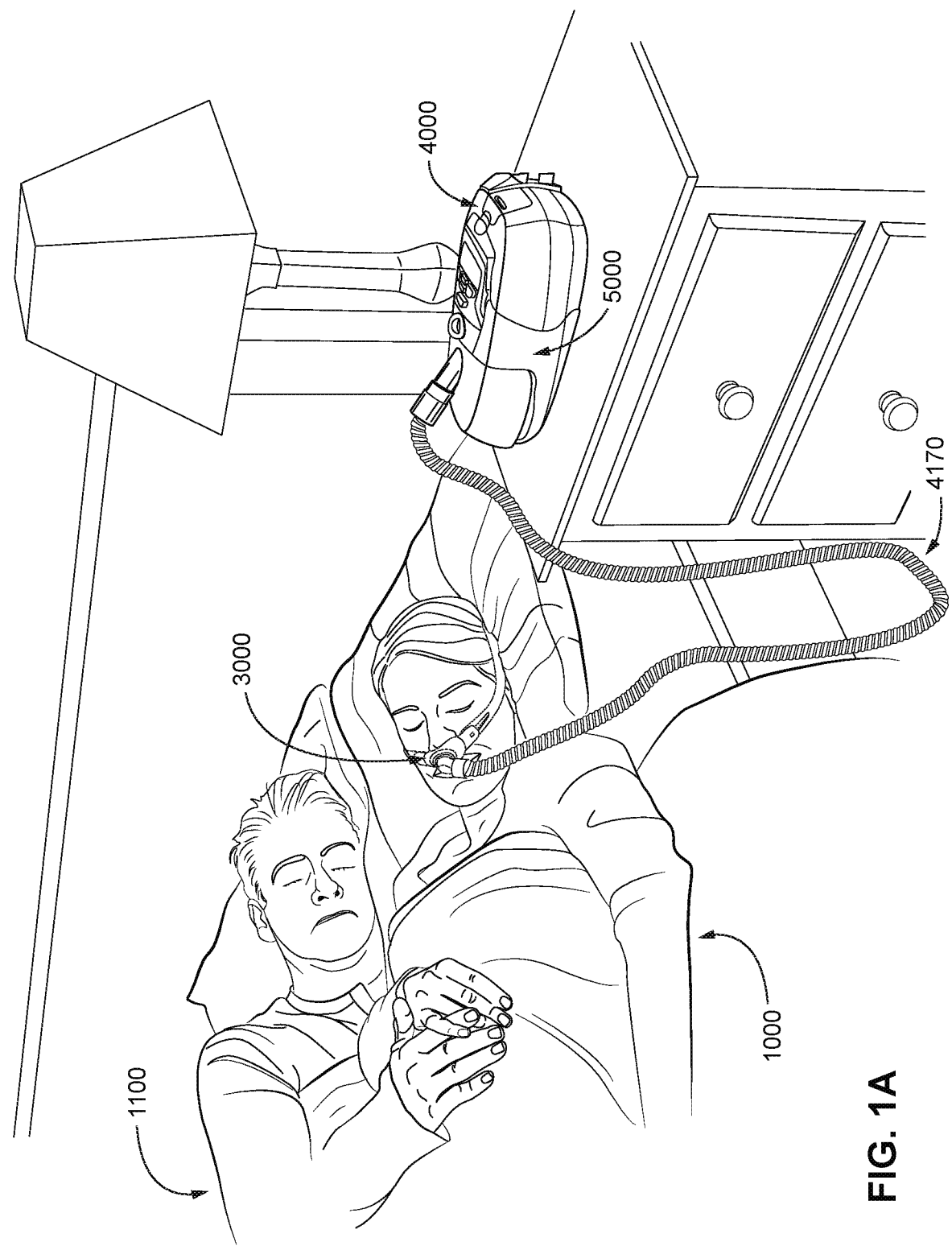
Figure 1C:
Figure 2A:
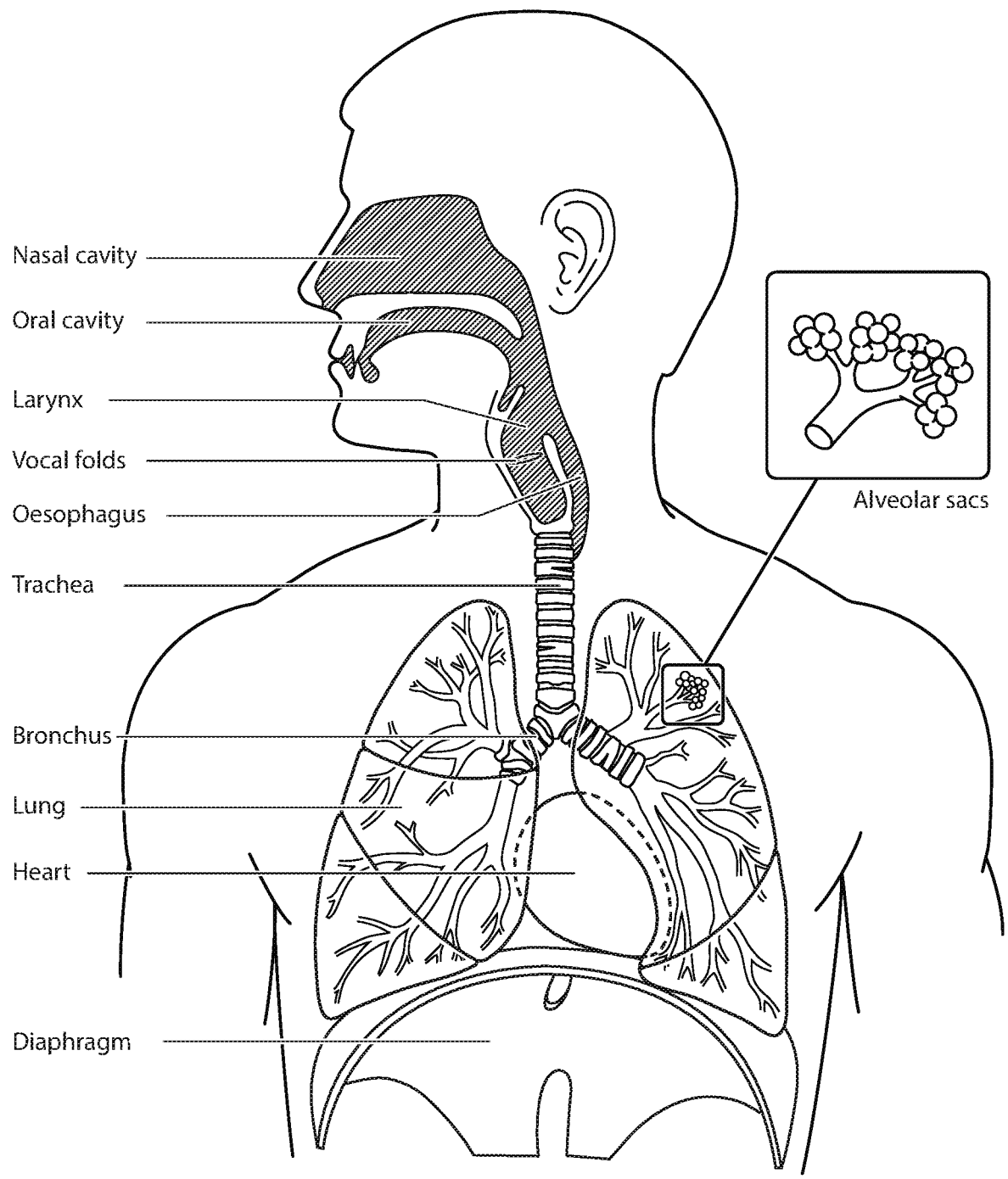
Figure 3A:
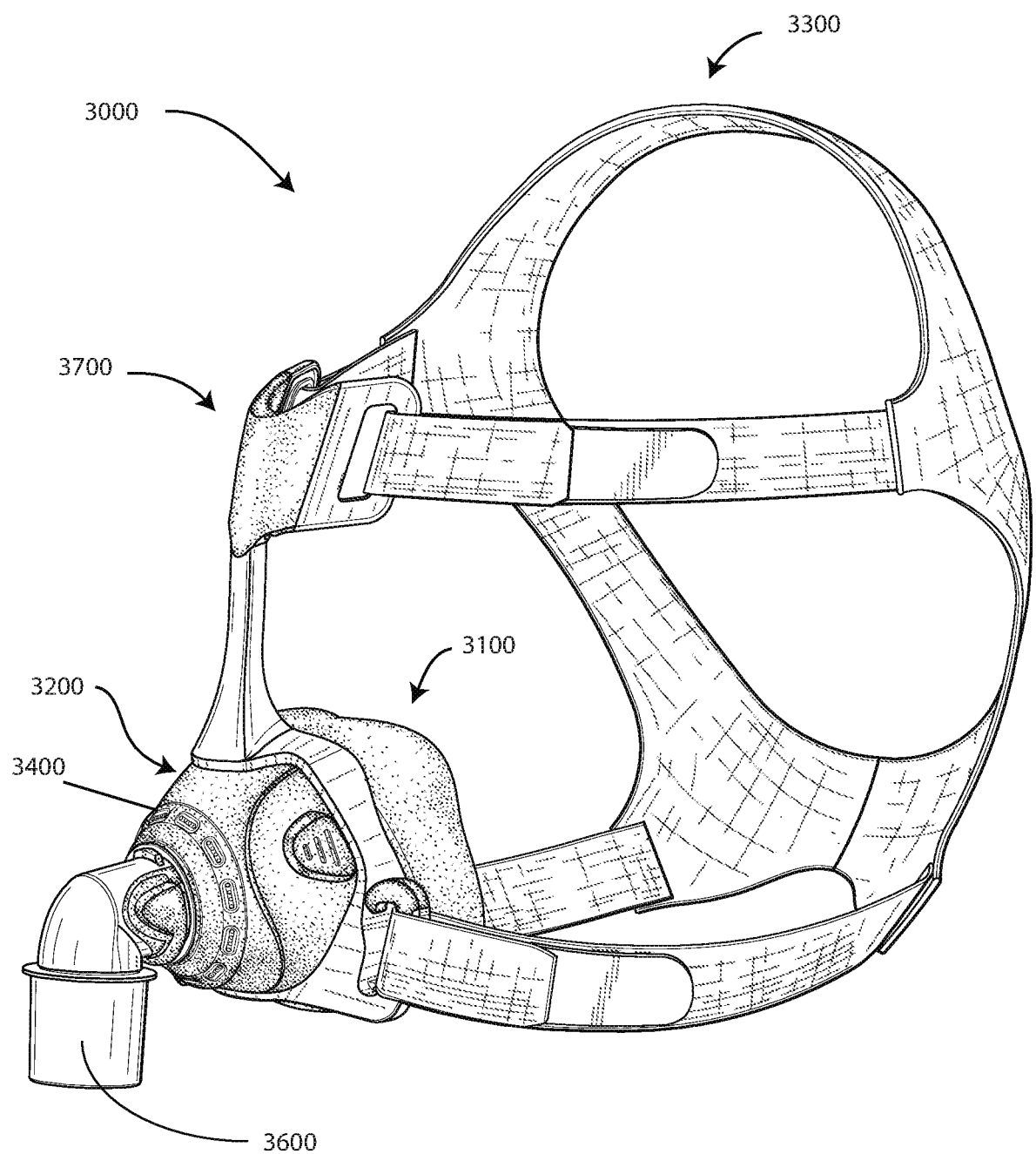
Figure 4A:
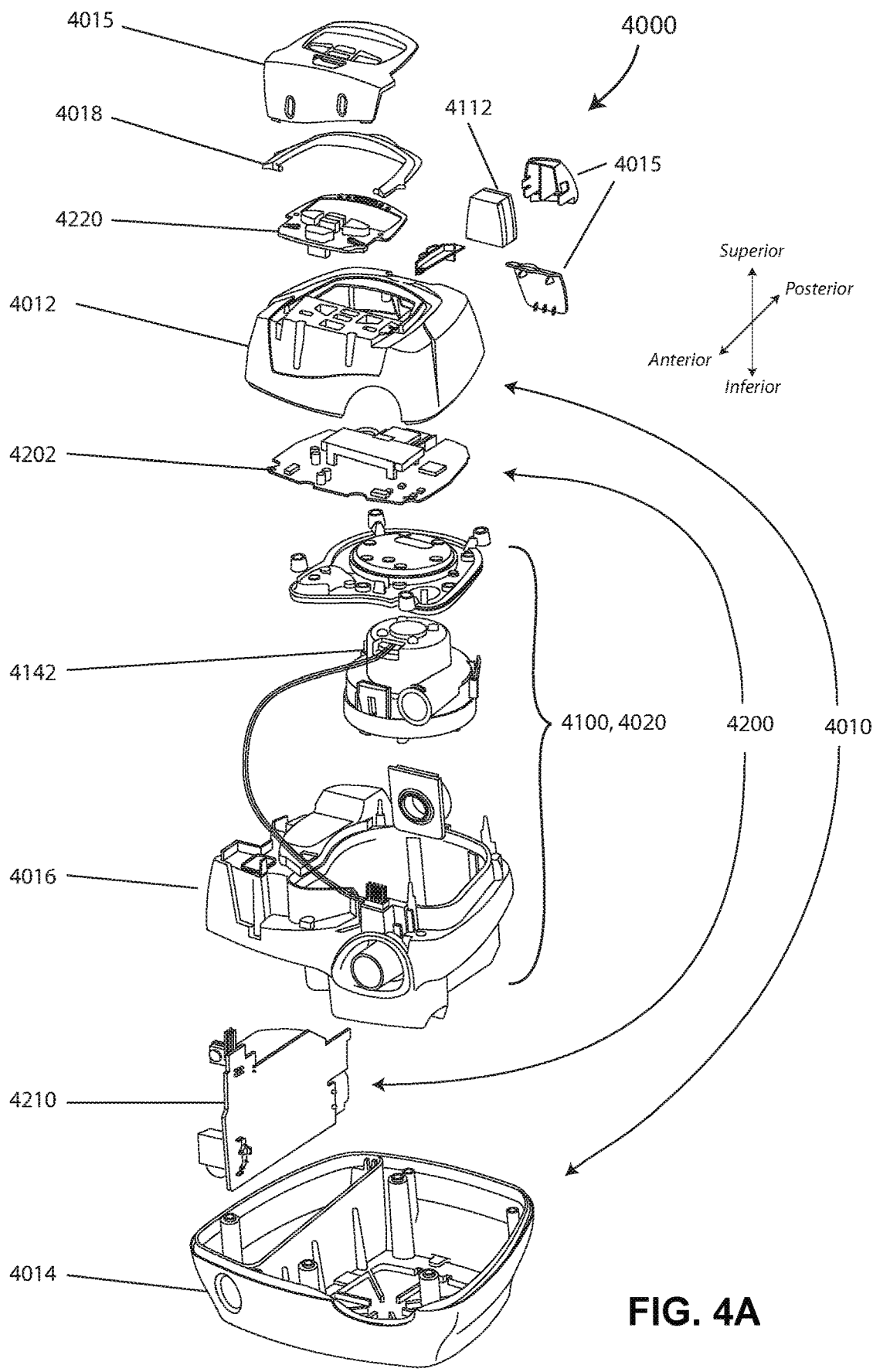
FIG. 4C is a schematic diagram of the electrical components of an RPT device in accordance with one form of the present technology.
FIG. 4D is a schematic diagram of the algorithms implemented in an RPT device in accordance with one form of the present technology.
FIG. 4E is a flow chart illustrating a method carried out by the therapy engine module of FIG. 4D in accordance with one form of the present technology.
Figure 4B:
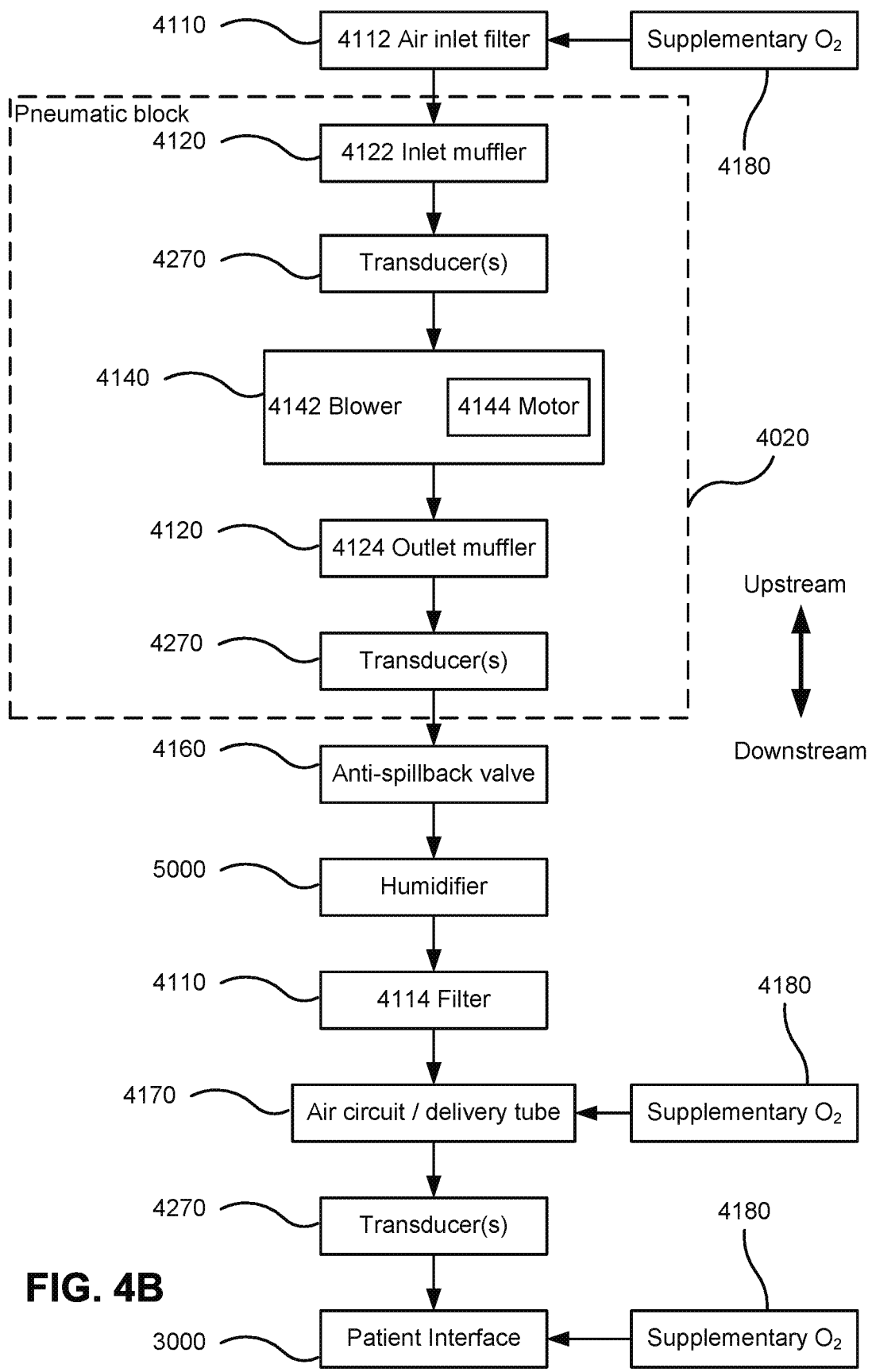
Figure 4C:
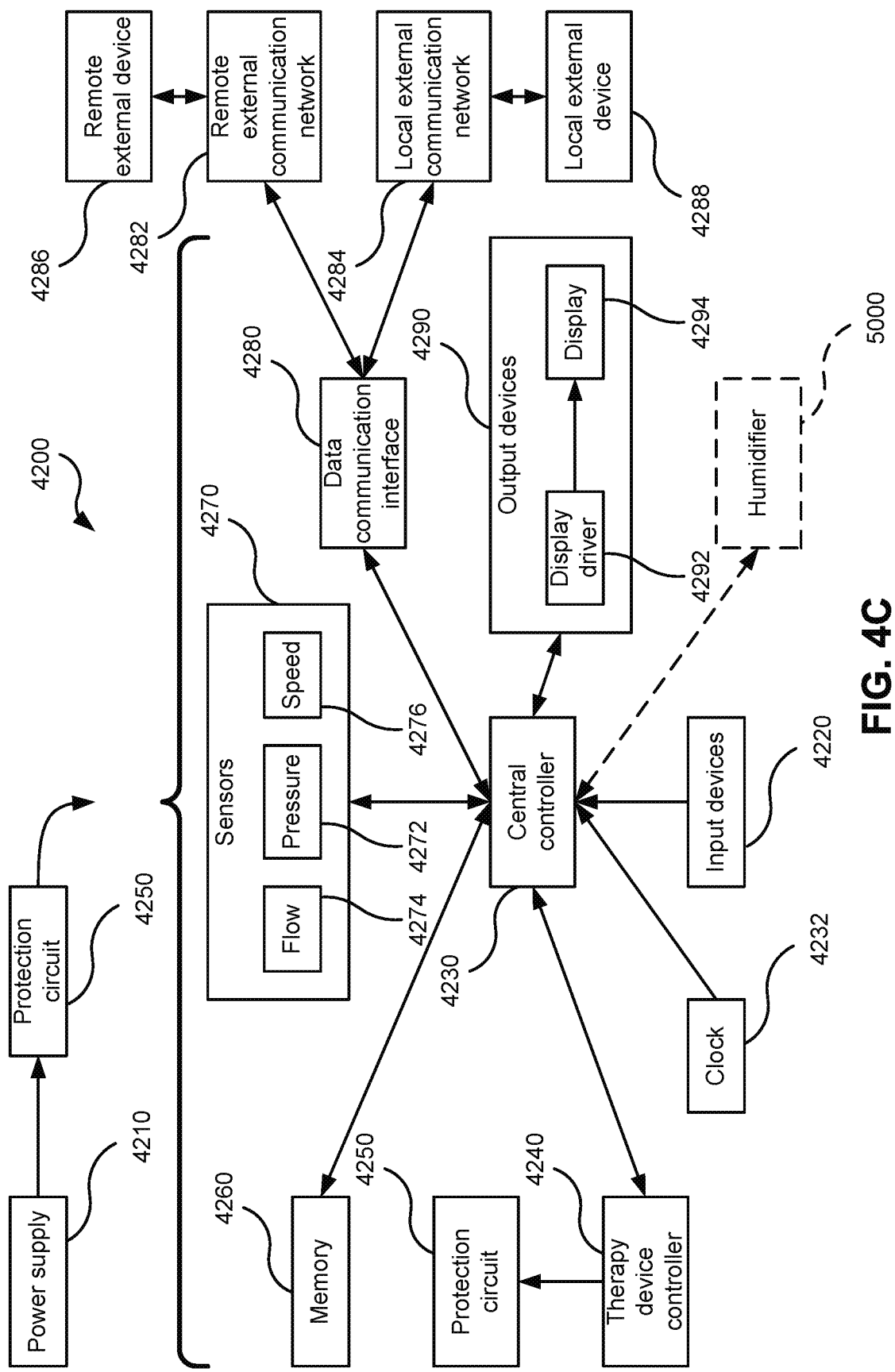
Figure 4D:
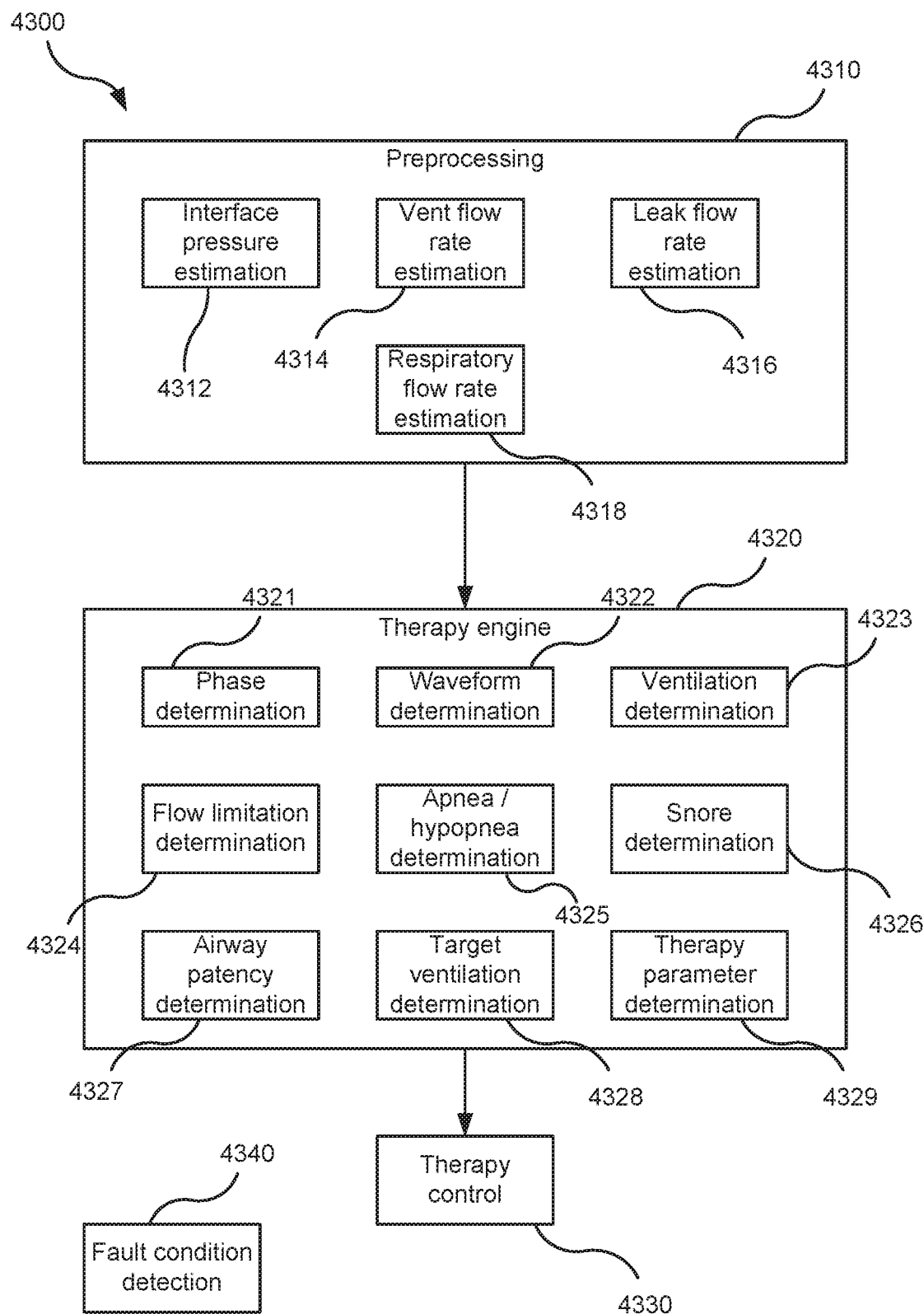
Figure 4E:
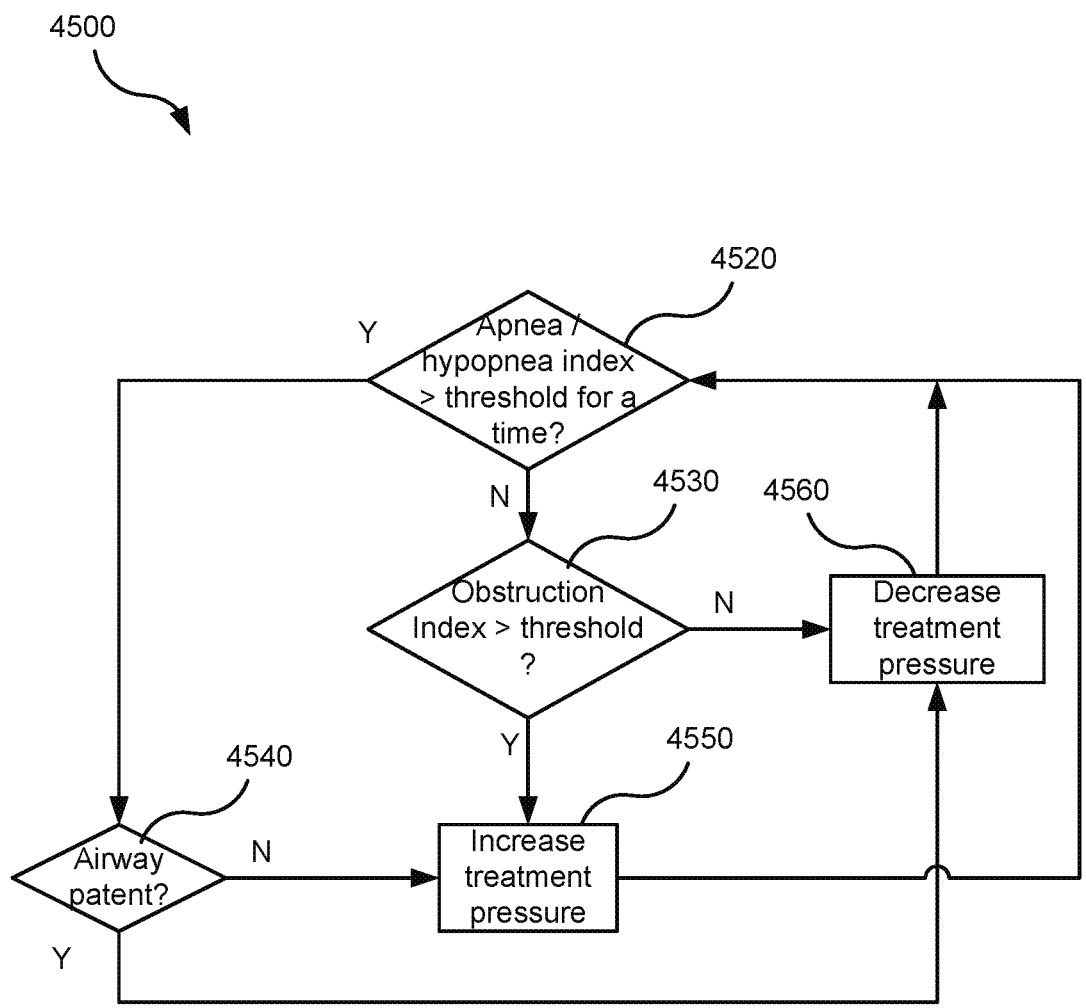

FIG. 4E is a flow chart illustrating a method 4500 carried out by the central controller 4230 to continuously compute the base pressure $P_0$ as part of an APAP therapy implementation of the therapy parameter determination algorithm 4329, when the pressure support A is identically zero.

The method 4500 starts at step 4520, at which the central controller 4230 compares the measure of the presence of apnea/hypopnea with a first threshold, and determines whether the measure of the presence of apnea/hypopnea has exceeded the first threshold for a predetermined period of time, indicating an apnea/hypopnea is occurring. If so, the method 4500 proceeds to step 4540; otherwise, the method 4500 proceeds to step 4530. At step 4540, the central controller 4230 compares the measure of airway patency with a second threshold. If the measure of airway patency exceeds the second threshold, indicating the airway is patent, the detected apnea/hypopnea is deemed central, and the method 4500 proceeds to step 4560; otherwise, the apnea/hypopnea is deemed obstructive, and the method 4500 proceeds to step 4550.

At step 4530, the central controller 4230 compares the measure of flow limitation with a third threshold. If the measure of flow limitation exceeds the third threshold, indicating inspiratory flow is limited, the method 4500 proceeds to step 4550; otherwise, the method 4500 proceeds to step 4560.

At step 4550, the central controller 4230 increases the base pressure $P_0$ by a predetermined pressure increment ΔP, provided the resulting treatment pressure Pt would not exceed a maximum treatment pressure Pmax. In one implementation, the predetermined pressure increment ΔP and maximum treatment pressure Pmax are 1 cmH$_2$O and 25 cmH$_2$O respectively. In other implementations, the pressure increment ΔP can be as low as 0.1 cmH$_2$O and as high as 3 cmH$_2$O, or as low as 0.5 cmH$_2$O and as high as 2 cmH$_2$O. In other implementations, the maximum treatment pressure Pmax can be as low as 15 cmH$_2$O and as high as 35 cmH$_2$O, or as low as 20 cmH$_2$O and as high as 30 cmH$_2$O. The method 4500 then returns to step 4520.

At step 4560, the central controller 4230 decreases the base pressure $P_0$ by a decrement, provided the decreased base pressure $P_0$ would not fall below a minimum treatment pressure Pmin. The method 4500 then returns to step 4520. In one implementation, the decrement is proportional to the value of $P_0$-Pmin, so that the decrease in $P_0$ to the minimum treatment pressure Pmin in the absence of any detected events is exponential. In one implementation, the constant of proportionality is set such that the time constant r of the exponential decrease of $P_0$ is 60 minutes, and the minimum treatment pressure Pmin is 4 cmH$_2$O. In other implementations, the time constant r could be as low as 1 minute and as high as 300 minutes, or as low as 5 minutes and as high as 180 minutes. In other implementations, the minimum treatment pressure Pmin can be as low as 0 cmH$_2$O and as high as 8 cmH$_2$O, or as low as 2 cmH$_2$O and as high as 6 cmH$_2$O. Alternatively, the decrement in $P_0$ could be predetermined, so the decrease in $P_0$ to the minimum treatment pressure Pmin in the absence of any detected events is linear.

5.8.2 Bi-Level Therapy

In other implementations of this form of the present technology, the value of amplitude A in equation (1) may be positive. Such implementations are known as bi-level therapy, because in determining the treatment pressure Pt using equation (1) with positive amplitude A, the therapy parameter determination algorithm 4329 oscillates the treatment pressure Pt between two values or levels in synchrony with the spontaneous respiratory effort of the patient 1000. That is, based on the typical waveform templates Π(Φ, t) described above, the therapy parameter determination algorithm 4329 increases the treatment pressure Pt to $P_0$+A (known as the IPAP) at the start of, or during, or inspiration and decreases the treatment pressure Pt to the base pressure $P_0$ (known as the EPAP) at the start of, or during, expiration.

In some forms of bi-level therapy, the IPAP is a treatment pressure that has the same purpose as the treatment pressure in CPAP therapy modes, and the EPAP is the IPAP minus the amplitude A, which has a "small" value (a few cmH$_2$O) sometimes referred to as the Expiratory Pressure Relief (EPR). Such forms are sometimes referred to as CPAP therapy with EPR, which is generally thought to be more comfortable than straight CPAP therapy. In CPAP therapy with EPR, either or both of the IPAP and the EPAP may be constant values that are hard-coded or manually entered to the RPT device 4000. Alternatively, the therapy parameter determination algorithm 4329 may repeatedly compute the IPAP and/or the EPAP during CPAP with EPR. In this alternative, the therapy parameter determination algorithm 4329 repeatedly computes the EPAP and/or the IPAP as a function of indices or measures of sleep disordered breathing returned by the respective algorithms in the therapy engine module 4320 in analogous fashion to the computation of the base pressure $P_0$ in APAP therapy described above.

In other forms of bi-level therapy, the amplitude A is large enough that the RPT device 4000 does some or all of the work of breathing of the patient 1000. In such forms, known as pressure support ventilation therapy, the amplitude A is referred to as the pressure support, or swing. In pressure support ventilation therapy, the IPAP is the base pressure $P_0$ plus the pressure support A, and the EPAP is the base pressure $P_0$.

In some forms of pressure support ventilation therapy, known as fixed pressure support ventilation therapy, the pressure support A is fixed at a predetermined value, e.g. 10 cmH$_2$O. The predetermined pressure support value is a setting of the RPT device 4000, and may be set for example by hard-coding during configuration of the RPT device 4000 or by manual entry through the input device 4220.

In other forms of pressure support ventilation therapy, broadly known as servo-ventilation, the therapy parameter determination algorithm 4329 takes as input some currently measured or estimated parameter of the respiratory cycle (e.g. the current measure Vent of ventilation) and a target value of that respiratory parameter (e.g. a target value Vtgt of ventilation) and repeatedly adjusts the parameters of equation (1) to bring the current measure of the respiratory parameter towards the target value. In a form of servo-ventilation known as adaptive servo-ventilation (ASV), which has been used to treat CSR, the respiratory parameter is ventilation, and the target ventilation value Vtgt is computed by the target ventilation determination algorithm 4328 from the typical recent ventilation Vtyp, as described above.

In some forms of servo-ventilation, the therapy parameter determination algorithm 4329 applies a control methodology to repeatedly compute the pressure support A so as to bring the current measure of the respiratory parameter towards the target value. One such control methodology is Proportional-Integral (PI) control. In one implementation of PI control, suitable for ASV modes in which a target ventilation Vtgt is set to slightly less than the typical recent ventilation Vtyp, the pressure support A is repeatedly computed as:

$$A = G \int (\text{Vent} - \text{Vtgt}) dt \quad (2)$$

where G is the gain of the PI control. Larger values of gain G can result in positive feedback in the therapy engine module 4320. Smaller values of gain G may permit some residual untreated CSR or central sleep apnea. In some implementations, the gain G is fixed at a predetermined value, such as −0.4 cmH$_2$O/(L/min)/sec. Alternatively, the gain G may be varied between therapy sessions, starting small and increasing from session to session until a value that substantially eliminates CSR is reached. Conventional means for retrospectively analysing the parameters of a therapy session to assess the severity of CSR during the therapy session may be employed in such implementations In yet other implementations, the gain G may vary depending on the difference between the current measure Vent of ventilation and the target ventilation Vtgt.

Other servo-ventilation control methodologies that may be applied by the therapy parameter determination algorithm 4329 include proportional (P), proportional-differential (PD), and proportional-integral-differential (PID).

The pressure support limits Amin and Amax are settings of the RPT device 4000, set for example by hard-coding during configuration of the RPT device 4000 or by manual entry through the input device 4220.

In pressure support ventilation therapy modes, the EPAP is the base pressure $P_0$. As with the base pressure $P_0$ in CPAP therapy, the EPAP may be a constant value that is prescribed or determined during titration. Such a constant EPAP may be set for example by hard-coding during configuration of the RPT device 4000 or by manual entry through the input device 4220. This alternative is sometimes referred to as fixed-EPAP pressure support ventilation therapy. Titration of the EPAP for a given patient may be performed by a clinician during a titration session with the aid of PSG, with the aim of preventing obstructive apneas, thereby maintaining an open airway for the pressure support ventilation therapy, in similar fashion to titration of the base pressure $P_0$ in constant CPAP therapy.

Alternatively, the therapy parameter determination algorithm 4329 may repeatedly compute the base pressure $P_0$ during pressure support ventilation therapy. In such implementations, the therapy parameter determination algorithm 4329 repeatedly computes the EPAP as a function of indices or measures of sleep disordered breathing returned by the respective algorithms in the therapy engine module 4320, such as one or more of flow limitation, apnea, hypopnea, patency, and snore. Because the continuous computation of the EPAP resembles the manual adjustment of the EPAP by a clinician during titration of the EPAP, this process is also sometimes referred to as auto-titration of the EPAP, and the therapy mode is known as auto-titrating EPAP pressure support ventilation therapy, or auto-EPAP pressure support ventilation therapy.

5.8.3 High Flow Therapy

In other forms of respiratory therapy, the pressure of the flow of air is not controlled as it is for respiratory pressure therapy. Rather, the central controller 4230 controls the pressure generator 4140 to deliver a flow of air whose device flow rate Qd is controlled to a treatment or target flow rate Qtgt. Such forms are generally grouped under the heading of flow therapy. In flow therapy, the treatment flow rate Qtgt may be a constant value that is hard-coded or manually entered to the RPT device 4000. If the treatment flow rate Qtgt is sufficient to exceed the patient's peak inspiratory flow rate, the therapy is generally referred to as high flow therapy (HFT). Alternatively, the treatment flow rate may be a profile Qtgt(t) that varies over the respiratory cycle.

5.9 Data Transmission and Gathering

Connected devices such as the RPT 4000 in FIG. 4A are capable of storing and sending varying levels of data. For example, the central controller 4230 in FIG. 4C or applicable device processor may send data to the external source 4286. Such data may include the data gathered by the sensors of the RPT 4000, such as the flow rate sensor 4272 or pressure sensor 4272, data gathered by exercise equipment sensors, such as speed and length of workout, data gathered by computer systems such as user interaction frequency and type with a user interface; data generated by the algorithms of the pre-processing module 4310 or other algorithms; or data generated by the algorithms of the therapy engine module 4320. Such data may be combined for analysis by algorithms that generate yet more data.

FIG. 8A shows a block diagram illustrating one implementation 7000 of a system according to the present technology, which may be an RPT system. The system 7000 may comprises a device 4000 configured to provide respiratory pressure therapy to a patient 1000, a data server 7010, and a computing device 7050 associated with the patient 1000 or user. The computing device 7050 may be co-located with the user 1000 and the device 4000 (such as an RPT device). In the implementation 7000 shown in FIG. 7A, the device 4000, the computing device 7050, and the data server 7010 are connected to a wide area network 7090 such as an internet, the cloud, or the Internet.

The connections to the wide area network may be wired or wireless. The wide area network may be identified with the remote external communication network 4282 of FIG. 4C, and the data server 7010 may be identified with the remote external device 4286 of FIG. 4C. The computing device 7050 may be a personal computer, mobile phone, tablet computer, or other device and may be incorporated into various equipment disclosed herein. The computing device 7050 may be configured to intermediate between the user (e.g. patient 1000) and the data server 7010 over the wide area network 7090. In one implementation, this intermediation is performed by a software application program 7060 that runs on the computing device 7050. The user program 7060 may be a dedicated application referred to as a "user application" that interacts with a complementary process hosted by the data server 7010. In another implementation, the user program 7060 is a web browser that interacts via a secure portal with a web site hosted by the data server 7010. In yet another implementation, the user program 7060 is an email client.

FIG. 8B contains a block diagram illustrating an alternative implementation 7000B of a system according to the present technology. In the alternative implementation 7000B, the device 4000 communicates with the user computing device 7050 via a local (wired or wireless) communications protocol such as a local network protocol (e.g., Bluetooth). In the alternative implementation 7000B, the local network may be identified with the local external communication network 4284 of FIG. 4C, and the user computing device 7050 may be identified with the local external device 4288 of FIG. 4C. In the alternative implementation 7000B, the user patient computing device 7050, via the user program 7060, is configured to intermediate between the user (e.g. patient 1000) and the data server 7010, over the wide area network 7090, and also between the device 4000 and the data server 7010 over the wide area network 7090.

In what follows, statements about the system 7000 may be understood to apply equally to the alternative implementation 7000B, except where explicitly stated otherwise.

The system 7000 may contain other devices (not shown) associated with respective users or patients who also have respective associated computing devices. Further, the system 7000 may include other monitoring or therapy devices that may be interfaced with the controller 4230 or the user computing device 7050.

The device 4000 may be configured to store in the memory 4260 data from each usage session delivered to the user (e.g. patient 1000). For instance, therapy data for an RPT session comprises the settings of the RPT device 4000 and therapy variable data representing one or more variables of the respiratory pressure therapy throughout the RPT session.

The device 4000 may be configured to transmit data to the data server 7010. As explained above, the transmission of the data is modulated based on different cases. In normal operation, low resolution data alone is transmitted. High resolution data may be transmitted in different cases, as will be explained below. The data server 7010 may receive the data from the device 4000 according to a "pull" model whereby the device 4000 transmits the data in response to a query from the data server 7010. Alternatively, the data server 7010 may receive the data according to a "push" model whereby the device 4000 transmits the data to the data server 7010 as soon as convenient after a session.

Data received from the device 4000 may be stored and indexed by the data server 7010 so as to be uniquely associated with the device 4000 and therefore distinguishable from data from any other device(s) participating in the system 7000.

In this example, the data server 7010 is configured to calculate different types of analytical data that may be of use to a clinician or system administrator. For example, usage data for each session may be determined from the data received from the device 4000. Usage data variables for a session comprise summary statistics derived by conventional scoring means from the variable data that forms part of the data.

Usage data may comprise one or more of the following usage variables:
- usage time, i.e. total duration of the session;
- apnea-hypopnea index (AHI) for the session;
- average leak flow rate for the session
- average mask pressure for the session;
- number of "sub-sessions" within the RPT session, i.e. number of intervals of RPT therapy between "mask-on" and "mask-off" events;
- other statistical summaries of the therapy variables, e.g. 95th percentile pressure, median pressure, histogram of pressure values;
- number of times using an, RPT device, on-demand service or other system per time period (e.g. days, week, month; and
- multi-session statistics, such as mean, median, and variance of AHI since the start of RPT therapy, trends in exercise duration, calorie burn, speed or other metrics; and
- others.

Other servers may be coupled to the network 7090 and obtain data based on the "push" or "pull" model described above. For example, a data server 7100 operated by a payee may receive data for different purposes such as determining compliance or predicting compliance for purposes of determining payment for therapy of the patient 1000 or other services for a user. A machine learning server 7200 may also receive data for purposes of learning or refining baselines for exceptional cases that require high resolution data as will be explained below. Alternatively, the machine learning server 7200 may learn optimal responses when exceptional cases are detected or the correct predictive data to be included in high resolution data in response to certain exceptional cases.

In an alternative implementation, the device 4000 calculates the usage variables from the data stored by the device 4000 at the end of each session. The device 4000 then transmits the usage variables to the data server 7010 according to the "push" or "pull" model described above.

In a further implementation, the memory 4260 in which the device 4000 stores the therapy/usage data for each session is in removable form, such as an SD memory card. The removable memory 4260 may be removed from the device 4000 and inserted into a card reader in communication with the data server 7010. The therapy/usage data is then copied from the removable memory 4260 to the memory of the data server 7010.

In still a further implementation, suitable for the alternative implementation 7000B of the system, the device 4000 is configured to transmit the therapy/usage data to the user computing device 7050 via a wireless communications protocol such as Bluetooth as described above. The user computing device 7050 then transmits the therapy/usage data to the data server 7010. The data server 7010 may receive the therapy/usage data from the user computing device 7050 according to a "pull" model whereby the user computing device 7050 transmits the therapy/usage data in response to a query from the data server 7010. Alternatively, the data server 7010 may receive the therapy/usage data according to a "push" model whereby the patient computing device 7050 transmits the therapy/usage data to the data server 7010 as soon as it is available after a session.

In some implementations, the data server 7010 may carry out some post-processing of the usage data, such as with one or more processors in communication with or included in the data server 7010. One example of such post-processing is to determine whether the most recent session is a "compliant session". Some compliance rules specify the required RPT device usage over a compliance period, such as 30 days, in terms of a minimum duration of device usage per session, such as four hours, for some minimum number of days, e.g. 21, within the compliance period.

A session is deemed compliant if its duration exceeds the minimum duration. The usage data post-processing may determine whether the most recent session is a compliant session by comparing the usage duration with the minimum duration from the compliance rule. The result of such post-processing is compliance data, such as a Boolean compliance variable, that forms part of the usage data. A further example of multi-session usage data is a count of compliant sessions since the start of RPT therapy or other types of sessions.

The data server 7010 may also be configured to receive data from the user computing device 7050. Such may include data entered by the user or patient 1000 to the user program 7060, or therapy/usage data in the alternative implementation 7000B described above.

The data server 7010 is also configured to transmit electronic messages to the user computing device 7050. The messages may be in the form of emails, SMS messages, automated voice messages, or notifications within the user program 7060.

The device 4000 may be configured such that its therapy mode, or settings for a particular therapy mode, may be altered on receipt of a corresponding command via its wide area or local area network connection. In such an implementation, the data server 7010 may also be configured to send such commands directly to the device 4000 (in the implementation 7000) or indirectly to the device 4000, relayed via the user computing device 7050 (in the implementation 7000B).

The data server 7010 hosts a process 7020, described in detail below, that is configured to increase or sustain the user's motivation to continue with therapy or other service. In broad terms, the process 7020 analyses data from the device 4000 and/or the patient computing device 7050 or user computing device 7050 to compute a quality indicator that is indicative of the quality of the most recent therapy session or other type of user session as disclosed herein. The process 7020 then communicates the quality indicator to the user or patient 1000, for example via the user program 7060 running on the user computing device 7050. The need to increase motivation may be detected by analysing low resolution data and high resolution data may be obtained to optimize the methods to increase or sustain the motivation of the patient.

The patient 1000 or user perceives the therapy or other usage quality indicator as a concise indicator of how their therapy, exercise or other sessions are progressing. The user or patient 1000 is thereby motivated to persevere with their therapy. It is known that tracking and measuring performance can be a strong motivator for a person to achieve their goals, and the therapy quality indicator serves as such a performance measure in the context of respiratory pressure therapy.

5.9.1 Prediction of Patient Compliance or Quitting with Respiratory Therapy

Studies have shown that up to 90% of patients prescribed respiratory pressure therapy have at least some problems meeting compliance rules. Examples, of such problems include difficulty in setting up an RPT device 4000, discomfort due to an ill-fitting or ill-adjusted patient interface 3000, lack of tolerance for the sensation of positive airway pressure at the prescribed level, excessive leaks causing noise or disruption to the patient or bed partner, and lack of improvement in subjective well-being. This leads to low compliance, lower reimbursement, and suboptimal health outcomes and higher overall long term healthcare cost for patients 1000, and additional health care costs in the form of exacerbated related conditions for non-compliant patients 100. For instance, in some countries, patients 1000 must meet a minimum level of compliance to be reimbursed. Accordingly, the inventors have developed technology to predict whether a patient 1000 will be compliant with therapy, and automatically intervene to improve compliance and ongoing therapy adherence & utilization.

Specifically, the disclosed technology and associated devices 4000 may implement automated systems that monitor usage to identify patients 1000 or other users likely to reduce usage and automatically intervene, including by notifying providers or the patient 1000 or user. This provides an opportunity to adjust therapy, or other relevant settings, switch to more appropriate equipment, correct any issues the patient 1000 or user may have with therapy or service, or provide other counselling to help increase patient 1000 or user compliance and long-term adherence outcomes or enrolment in the service.

As an example, it has been determined that the trend of usage data may be especially predictive of future compliance and continuous usage rates. Therefore, in certain forms of the present technology, usage data 9045 output from a device (e.g., an RPT device 4000) may be monitored to determine when a patient 1000 or user is likely to terminate therapy or reduce usage by a specific amount.

FIG. 9 illustrates an example of a process for predicting whether a patient or user will reduce or cease usage of an RPT device 4000. First, a patient 1000 may initiate a session or service (e.g., RPT therapy session) by turning on the device 4000, using the device (e.g, wearing the device for a therapy session), and then turning the device off (e.g., and/or removing the mask once it is finished).

Upon finishing of a session 9000, the RPT device 4000 may output usage data 9010 to an external source, for instance over a network to a server and a database. In other examples, the device 4000 may locally store the usage data 9045 and send the data to an external source after a week of usage data 9045 is stored, for example. In further examples, the device 4000 may store the data and processes the usage data locally on a processor 4230 and memory 4360. The usage data 9045 may contain various types of information including those disclosed above.

In some examples, demographic data, profile data, healthcare provider, machine type, and other data may be utilized in the models. This data may be stored locally on a device 4000, or stored separately in a database referenced to a patient ID for efficient retrieval and updating of algorithms. This data may not need to be updated each time a model or algorithm is updated, and therefore may be stored separately in some examples. This may also save on bandwidth for sending the usage data from the device 4000.

Additionally, after the usage data 9045 is output and stored, the disclosed technology may identify a time window of previously stored usage data 9020. For instance, the disclosed technology may identify the previously stored usage data 9020 recorded in the prior week, two weeks, three weeks or other suitable time frame to identify a trend of usage using an algorithm.

Next, the disclosed technology may process the data to determine the likelihood a patient 1000 or user will decrease (or maintain) usage levels within a future time window 9030. For instance, the disclosed technology may determine the percentage likelihood a patient 1000 or user will decrease usage from four hours to two hours within two weeks, or from three sessions to one session within two weeks. In other examples, the disclosed technology may determine the percentage likelihood the patient 1000 or user will cease usage within two weeks, three weeks, one week, or other predictive time frame. In some examples, the disclosed technology will process the data and predict the amount (of average hours per night for example) the patient 1000 or user will use the device 4000, system and/or service in a future time window, without necessarily predicting whether or not the patient 1000 or user will decrease usage.

The disclosed technology may utilize various algorithms to determine the percentage chance a patient 1000 or user will decrease or cease usage (or maintain current usage levels) within a certain time window. The platform may utilize various sources of data including: (1) usage data 9045 (including the latest session and historical usage data and other types of data disclosed above), (2) demographic data 9035 (including the patient's age), and (3) device type 9055 (including the device type, model, and manufacturer, including RPT device, computing device, or other device), and other suitable data. In some examples, a health care provider may also be input data. As described above, the usage data 9045 may be output from a device 4000 and other sources of data may be stored on a separate database. In other examples, all of the data may be stored on a memory of a device 4000.

Next, the disclosed technology may first calculate various features from the data including the data from the usage sessions within the prior usage time window. For instance, the disclosed technology may determine the pattern of non-usage days, the average hours of usage, the average hours of use by week, the age, the engagement with associated online platforms, and other factors. These features may be calculated on a weekly basis, to determine the weekly trend of each of these features, in some examples.

In certain forms of the present technology, these features will then be input into various algorithms to output the percentage likelihood the patient 1000 will decrease usage by a certain amount within a certain time window 9030. For instance, the system may analyse the features with logistical regression, linear regression and/or random forest algorithms. In some examples, where the output is a binary classification—a logistical regression, decision tree, random forest, Bayesian network, support vector machine, neural network, or probit model may be utilized to output a probability the input features result in the patient 1000 terminating therapy. In other examples, machine learning algorithms and combinations of algorithms may be utilized to classify inputs into usage categories. This may include linear classifiers (logistical regression, naïve Bayes classifier), support vector machines, decision trees, boosted trees, random forest, neural networks, stochastic gradient descent, nearest neighbours, and others.

In addition, other machine learning algorithms may be utilized. In certain examples, a decision tree may be utilized to determine which pre-trained machine learning algorithm to apply. For instance, depending on the age cohort the patient 1000 or user belongs to, it may utilize different algorithms. In other examples, different providers or different types of devices 4000 may have different algorithms trained with data from those providers, for example. In other examples, the algorithm may output a binary determination of whether the patient 1000 or user is likely to quit, or the amount of usage bracket the patient 1000 or user will likely fit into (e.g. 4-2 hours, 2-0 hours, or ceasing usage).

Next, the disclosed technology may output an indication that the patient 1000 or user is likely to quit or reduce usage within a certain time window if the output percentage of the algorithm crosses a threshold 9040. This may include flagging the patient 1000 or user on an internal database of medical records, sending notifications to associated computing devices, servers, or the display 4294 of the device 4000. This would allow a health care provider to contact the patient 1000 or user or initiate various action steps discussed below.

5.9.2 Action Steps to Intervene if Lower Usage Predicted

In certain forms of the present technology, the notification may trigger an action to improve therapy 9050 or to reduce the probability the patient 1000 or user will terminate or reduce therapy or other service. For instance, patients 1000 or user end to terminate or reduce their usage for many reasons including therapy acclimation challenges, problems with equipment management, environmental factors and motivational issues. Some of the following reasons: (1) size or fit of the patient interface 3000 is inappropriate, (2) patients 1000 are not accustomed to wearing an RPT device 4000 while sleeping, (3) patients 1000 have difficulty breathing forced air, (4) a leaky patient interface 3000 which dry out the patient's 1000 nose or mouth, (5) excessive noise, (6) loud exercise equipment, (7) pain or aches, (8) or others.

Accordingly, the action step would most optimally would address the reason the patient 1000 or user intends to reduce or terminate therapy or other service. Thus, the disclosed technology may first apply various workflows or algorithms to determine the reason the patient 1000 or user may reduce or terminate usage. For instance, the disclosed technology may send a notification or a request to the display 4294 on the device 4000 providing a menu or options and requesting the patient 1000 or user to indicate which aspects of the therapy or other service the patient 1000 or user dislikes or are not effective.

The notification could also be a text, email, pop up notification on a mobile device, or other types of notifications. In some examples, depending on the probability of termination of therapy or other service, or the classification of usage, the notification frequency or content may change to increase motivation. In some examples, the menu could provide options for common issues that patient 1000 or user could select. This could then provide further remedial options to the patient 1000 or user, based on their selection, that would attempt to correct the patient's or user's difficulty with therapy or other service disclosed herein. In some examples, this may include display a video to a patient 1000, user or other content to help a patient 1000 or other user use the device 4000 if they are having difficulty using it.

In some examples, the current technology may use machine learning or other algorithms to estimate the reason patient 1000 or user is likely to quit. This may include monitoring certain aspects of sessions or the device 400 that are known to likely increase the chances a patient 1000 or user may terminate therapy. In some examples, the determination a patient 1000 or user may terminate therapy or reduce usage will trigger an analysis of other metrics that may be analysed to determine the highest probability reason the patient 1000 or user may quit. For instance, the leak flow rate, noise, respiratory events, sleep score, and other variables may be analysed to determine which has the highest deviation from normal, successful patients 1000 or users. Then, the disclosed technology may ask the patient 1000 or user questions starting with the highest probability identified reason for reduction of the service (e.g. respiratory therapy), and make appropriate interventions as detailed below. In some examples, the determination of the likely reasons may take into account demographic information (known the certain age cohorts have trouble using the device or its features). Following are a list of action steps that could be taken, and monitoring or other algorithms that may automatically determine when to take those steps.

Change Service Settings

In response to prompts on the RPT device 4000 or an associated app or software program on a computing device, the patient or clinician 1000 or user may input selections on the display or via a cloud management system 4294 that indicate that there is high leak from the patient interface, the patient is having trouble falling asleep or repeatedly waking during the night, their Sleep Disorder Breathing is not being effectively treated or is experiencing other therapy related issues leading to non-efficacious treatment. Accordingly, the current technology may prompt the patient 1000 with options to change the therapy settings 9065 on the RPT device 4000. Once those options are selected, the device that receives the patient input may send instructions to the controller of the RPT device 4000 to implement the changes.

Ramping Pressure while Patient Falls Asleep

Some patients 1000 flagged for reduction of usage may indicate that they are uncomfortable with high pressure and are not easily able to fall asleep (e.g., in response to a notification with a query regarding the same). The current technology may then present an option to the patient 1000 to select "RAMP" features that implements protocols on the RPT device 4000 to slowly increase the base pressure until the patient 1000 falls asleep when initiating therapy.

In some examples, the usage data 9045 may indicate the patient 1000 is removing the device within the first hour of turning it on, or some other threshold indicating the patient 1000 is having trouble falling asleep. Accordingly, the current technology may automatically suggest the RAMP feature if processing of the usage data 2045 indicates that the patient 1000 is discontinuing use within a short time window for instance 30 minutes, or within an hour. Additionally, the current technology may adjust the ramping feature to have an even lower initial pressure to aid a patient 1000 in falling asleep if the processed usage data 9045 identifies stopping early in usage (or low hours of usage per session, for instance).

Pressure, Expiratory Pressure Relief & Therapy Mode Adjustment

In some examples, the patient 1000 may wake up frequently, potentially indicating that the therapy settings are not optimal once the patient 1000 is asleep. In this example, a patient notification and input may be less valuable, because the patient 1000 may not consciously be aware of the therapy settings while they are asleep. Accordingly, certain algorithms may be utilized (as disclosed herein) to identify disordered sleep, breathing, or other sleep issues, and automatically adjust the therapy and breathing comfort settings. This also may include other adjustments to therapy modes, including APAP versus CPAP, and others.

Bi-Level Positive Airway Pressure

In some examples, the current technology may change the inspiratory pressure delivered to the patient 1000 if the patient 1000 indicates they are uncomfortable with the inspiratory pressure. In other examples, this may be offered as a mode to try with the patients 1000, perhaps if the patient 1000 is unaware of why they the therapy makes the uncomfortable.

Humidification

In some examples, the patient 1000 may select input that indicates that their mouth or nose is too wet or to dry. Once the current technology receives this input from the patient 1000, it may automatically recommend the humidification level be increased or decreased.

In other examples, if the patient 1000 provides input that they have a dry mouth or dry nose, the current technology may automatically determine whether the leak flow rate Qv is over a threshold that indicates humidity should be increased. For instance, once the current technology receives input that a patient 1000 indicates they have a dry mouth, the current technology or RTP device 4000 may automatically query or initiate the leak flow rate estimates 4316 to determine whether it is over a threshold.

Patient Interface Fit or Type of Device

In response to prompts on the RPT device 4000 or an associated app or software program on a computing device, the patient or clinician 1000 may input selections on the display 4294 that indicate their mouth is dry, the fit of the patient interface 3000 is not optimal (e.g. their face hurts). For instance, the patient 1000 may indicate they feel a leak between the skin and patient interface 3000, or other issues with the fitting of the device 9075 including as described herein. As described above, the leak flow rate estimation 4316 module may determine that there are issues with leaking through the patient interface 3000.

Accordingly, the current technology may prompt the patient 1000 to determine whether they feel the fit of the patient interface 3000 is wrong, and specifically if it feels to small or too large. Accordingly, the current technology may then recommend a replacement patient interface 3000 for the patient 1000 based on their data profile indicating their current patient interface 3000 and issues with the fit.

In some examples, the current technology may prompt the patient 1000 to indicate the portions of the face in contact with the patent interface 3000 that are uncomfortable. For instance, the current technology may request that the patient 1000 click on a diagram of the face to indicate the positions that are unconformable around the seal forming structure 3100, the positioning and stabilising structure 3300, or other portions of the patient interface 3000. Then, based on the uncomfortable positions and the platform may recommend an alternative patient interface 3000.

In some examples, the patient interface 3000 may include sensors on the positioning and stabilising structure 3300 to determine how tight the straps are, for instance. In some examples, this may include a simple tension assessment or pressure between the straps and patient 1000 head. This information may be compared to average tensions and pressures to provide a recommendation to a patient 1000 to loosen or tighten the positioning and stabilising structure 3300, or to change the size.

Noise

Noise is a frequent reason why patients 1000 discontinue therapy, including at the request of their sleeping partner. In response to prompts on the RPT device 4000 or an associated app or software program on a computing device, the patient 1000 or clinician may input selections on the display or cloud software 4294 that indicate the noise is too excessive or their partner feels the noise is too excessive. In that example, the current technology may perform a diagnostic check to determine whether the RPT device 4000 itself and all of its passageways and vents are creating more noise than the standard amount.

For instance, the current technology may assess whether the environmental noise is from the RPT device 4000 deviates from the average or expected noise levels.

Accordingly, the current technology and/or RPT device 4000 may include an acoustic sensor that senses ambient noise, RPT device 4000 related noise, and other forms of noise. In some instances, a machine learning algorithm may be employed to classify the types of noise, and identify a level of RPT device 4000 related noise (or "vent" noise and separate it from patient 1000 snoring and other ambient noise) and compare it to standard values. If those values are over a threshold, the current technology may recommend maintenance, resupply of parts, or other remedial measures.

In other examples, the current technology may automatically alter therapy settings within a range and optimize the settings to reduce noise if the patient 1000 indicates noise is the primary issues.

Type of Therapy

In response to prompts on the RPT device 4000 or an associated app or software program on a computing device, the patient 1000 or clinician may input selections on the display 4294 or cloud software that indicate they are dissatisfied with an RPT device 4000 based therapy in general and would rather have a different type of therapy 9085. In other examples, the usage data 9045 may be so low that the current technology recommends a different type of therapy, or the patient 1000 may have failed to engage in therapy using an RPT device 4000 after many different recommendations and actions taken by the current technology. In this instance, the current technology may recommend that the patient 1000 use an additional or supplemental form of therapy. For instance, the system may ask the patient 1000 if he or she would prefer a Mandibular Repositioning Device or cognitive behavioural therapy.

5.9.3 Example 1: Therapy Termination Predictor

The disclosed technology has been utilized on anonymized data sets from patient data to test whether specific logistical regression and random forest algorithms could predict when patients 1000 are likely to terminate therapy accurately. It has been discovered that the current technology can predict whether a patient 1000 will reduce or terminate usage of a respiratory therapy device (e.g. CPAP) within a two-week time window with 90% accuracy (on average) with these algorithms. This was confirmed by testing the current technology at twenty different patient cohorts, each with an installation based of 4,000-26,000. In one example the current technology identified over 40 patients a week as likely to terminate therapy from one cohort of about 16,000 patients.

Feature Set

In this example, the usage data 9045 was first pre-processed to identify target features for processing by the random forest and logistical regression algorithms. First, the current technology determined the time window of data to consider and the prediction window. As illustrated in FIG. 10, the current technology identified usage sessions occurring three weeks prior to the current time/date. Each usage session data collection may have included some combination or permutation of the following data information:

Date/time stamp;
Start therapy time, Stop therapy time;
Total therapy time
Therapy and Sensor Data (e.g. respiratory events identified, therapy settings, etc.); and
Patient ID.

This data may have been output from the RPT device 4000 (e.g. usage data, and therapy data), and other parts of the data may have come from a provider database). Next, each session data identified was processed to identify usage features that could be entered into the algorithms. For instance, the following table illustrates an example set of usage features determined based on the session data that was utilized in the studies:

| Variable | Description |
| --- | --- |
| NZD1,NZD2,NZD3 | Number of non-zero use days (week1, week2, week3 from forecasting time point) |
| NZUse1,NZUse2,NZUse3 | Average non-zero usage (hours) (week1, week2, week3 from forecasting time point) |
| NZSD1,NZSD2,NZSD3 | Standard Deviation of non-zero usage (week1, week2, week3 from forecasting time point) |
| NDS | Number of days since the beginning of therapy (till forecasting time point) |
| AGE | Age |

Additionally, features may include whether the user as enrolled in a patient engagement or therapy management software platform (or app). These features where then extracted from a sample data set and output as the features below for different patients 1000.

| AGE_NBR | PATIENT APP | NZD3 | NZUse3 | NZSD3 | NZD2 | NZUse2 | NZSD2 | NZD1 | NZUse1 | NZSD1 | NDS |
| --- | --- | --- | --- | --- | --- | --- | --- | --- | --- | --- | --- |
| 63 | 0 | 2 | 161 | 224 | 7 | 265 | 44 | 7 | 270 | 34 | 103 |
| 51 | 1 | 4 | 235 | 145 | 0 | NA | NA | 4 | 312 | 60 | 65 |
| 58 | 0 | 5 | 243 | 117 | 2 | 210 | 156 | 7 | 321 | 64 | 98 |
| 54 | 0 | 5 | 73 | 53 | 3 | 140 | 83 | 4 | 32 | 38 | 36 |
| 61 | 0 | 3 | 303 | 18 | 4 | 307 | 65 | 3 | 300 | 69 | 252 |
| 60 | 0 | 1 | 8 | NA | 0 | NA | NA | 0 | NA | NA | 24 |

The data was the processed using a logistical regression algorithm trained using prior data with true drop data (whether the patients 1000) actually dropped therapy. Through manipulation of the models, the studies revealed that some of the predictive features included: (1) number of non-zero use days (sessions) ("NZD"), (2) the average non-zero use ("NZUse"), and (3) the standard deviation of non-zero use ("NZSD"). Accordingly, in some examples, logistical regression algorithms may be developed that utilized these three features or other combinations of features.

Processing Algorithms

In this study, the trends of usage based on these features were processed using random forest and logistical regression algorithms, to output probability that each patient 1000 would terminate usage within a two-week time period. This included examining the trends of the features on a weekly basis (features for an entire week compared with the following weeks to identify a trend). Additionally, in this example, logistical regression models were created for each day in the prediction window. Each of these models were trained using a three-week window prior to the day the model predicts. Thus, for training data, for the patients 1000 that ended up terminating therapy, a separate model can be trained using a three-week window of prior usage data that ends: (a) 1 day prior to termination, (b) 2 days prior to termination, etc. so that in this case 14 models were trained because the termination prediction window is two weeks in this case.

Next the 14 models were trained using data from patients 1000 that did not terminate therapy. These 14 models where trained with different time windows of usage data (as in the termination data) starting from the last day the patient 1000 used the device (rather than the day of termination) up until 14 days prior to the last day. Accordingly, after training the 14 models with both termination and non-termination patients, they could be utilized to predict the probability of termination for new patients 1000.

Therefore, in this case 14 models where created, so that they could be applied to usage data and determine a probability of termination each day. Then, by combining the probabilities for the 14-day period, a total probability of termination can be determined within a future two-week window for each patient 1000.

Following is an example of some of the raw data, the probability indicated for each patient 1000 (one anonymous patient per column) and whether they actually terminated within two weeks ("True Drop"):

| Score | True |
|---|---|
| 0.0716 | 0 |
| 0.3418 | 0 |
| 0.0865 | 0 |
| 0.2484 | 0 |
| 0.3817 | 0 |
| 0.3045 | 0 |
| 0.6334 | 1 |
| 0.9748 | 1 |
| 0.9827 | 1 |
| 0.9788 | 1 |
| 0.9269 | 1 |
| 0.97 | 1 |

This study provided evidence that the disclosed platform could predict termination of therapy by a patient 1000 within a two-week window with a range of 88%-93% accuracy. These surprising results will be extremely beneficial to health care providers, so that they can intervene prior to a patient 1000 discontinuing therapy. For instance, once a patient has actually made the decision to terminate therapy, intervention is much more difficult. Accordingly, some of the advantages of this technology are derived from the fact that termination is predicted rather than monitored or detected. Rather than low usage or compliance alerts, this platform has the potential to predict low compliance and termination in the future. This will likely result in a much higher compliance and retention rate, and vastly improved outcomes for patients 1000 with sleep disorders.

5.9.4 Example 2: Therapy Compliance Predictor

The disclosed technology has also been utilized on data sets from health care providers to test whether specific linear and logistic regression algorithms could predict whether patients would remain compliant within a future time window. This is advantageous, because in some countries, reimbursement is dependent on past compliance. For instance, the reimbursement of a future month may be contingent on a level of compliance that meets a threshold for the previous month (e.g. the compliance for a past 28-day period may determine reimbursement for a future 28-day period). In some countries, reimbursement may only be based on compliance after an initial ramping up period (e.g. 10, 13, 14 or 15 weeks).

Accordingly, for some countries, it may be advantageous to predict whether a patient 1000 will be compliant for the next one, two, three, four, eight weeks, or other time period depending on local regulations. In this example, the disclosed technology was utilized to determine whether compliance could be predicted for a future 28-day period based on usage data for the past 28 days. Particularly, the disclosed technology predicted whether a patient's 1000 average usage for the next 28 day periods would be:

0-2 hours per day "[0,2]"
2-4 hours per day "[0,4]"
>4 hours per day "[4,24]'

It has been discovered that the correlation of usage among consecutive four week intervals is very high (0.9). Accordingly, the average usage of the previous four weeks may be utilized to estimate usage of the next four-week interval. For instance, the following equation is an example of how this could be determined:

$$\text{Usage}(t+1) = a + b \cdot \text{Usage}(t) + \text{error}$$

Specifically, in this example, the following features were processed from the data to estimate compliance in a 28-day period:

(1) U1: Average usage of the first three weeks of previous 28-day interval
(2) U2: Average usage of the last week of previous 28-day interval
(3) NOZERO_DAYS: Number of nonzero use days of previous 28-day interval
(4) SD_NZ: Standard deviation of nonzero usage of previous 28-day interval
(5) Interval: How many 28-day-intervals since the beginning of therapy
(6) Age These features were identified from the various sources of data as disclosed herein. Next, these features were processed in a first model using the following multiple linear regression model:

$$U = a + b \cdot U1 + c \cdot U2 + d \cdot \text{NOZERO\_DAYS} + e \cdot \text{SD\_NZ} + F \cdot \text{Age} + g \cdot \text{Interval} + \text{error}$$

In some examples, the interval feature may be dropped and the model should be trained for every interval (every 28-day period following initiation). The interval data may be obtained from the setup data output from the RTP device 4000.

The model above (or additional models) may be trained with data output from RPT devices 4000, profile data, and other patient 1000 data. This includes true historical usage data and other data from various 28 day intervals (in this example). The model can be trained by feeding training data from two consecutive 28 day intervals from true historical data for example.

In this example, the model performed well, but it was determined that the accuracy could be improved for some classes between 28 day intervals:

| T/P | [0,2) | [2,4) | [4,24] |
|---|---|---|---|
| [0,2) | 312 | 189 | 47 |
| [2,4) | 86 | 497 | 325 |
| [4,24] | 18 | 247 | 4385 |

Accordingly, a second model was developed to train a logistical regression algorithm to separate the data into [0.2] and [2,24] classes. Then, this model could be fit on the patients with predictions falling into [0,2] and [2,4] from the first model and reclassify them with the second model. The second model using a logistical regression equation with the same features as above. Using this process increased the accuracy of the prediction and the following results were demonstrated for the 28 day interval from the third to fourth week:

| T/P | [0,2) | [2,4) | [4,24] |
|---|---|---|---|
| [0,2) | 486 | 15 | 47 |
| [2,4) | 86 | 497 | 325 |
| [4,24] | 18 | 247 | 4385 |

This greatly improved the prediction accuracy of the [0,2] class. Accordingly, continual improvements can be made to increase the accuracy of each class, so that the disclosed technology could reliably classify the usage predictors of a patient with close to 90% accuracy.

The most important features identified for compliance prediction included U1, U2, NOZERO_DAYS, SD_NZ, Age, and Interval. The features that were not as important (at least in this model) includes AHI (Apnea-hypopnea index), LEAK (leak flow rate), and patient App indicator.

5.10 Glossary

For the purposes of the present technology disclosure, in certain forms of the present technology, one or more of the following definitions may apply. In other forms of the present technology, alternative definitions may apply.

5.10.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including cmH$_2$O, g-f/cm$^2$ and hectopascal. 1 cmH$_2$O is equal to 1 g-f/cm$^2$ and is approximately 0.98 hectopascal (1 hectopascal=100 Pa=100 N/m$^2$=1 millibar~0.001 atm). In this specification, unless otherwise stated, pressure is given in units of cmH$_2$O.

The pressure in the patient interface is given the symbol Pm, while the treatment pressure, which represents a target value to be achieved by the interface pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.10.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.10.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.11 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

The invention claimed is:

1. A system for treating a respiratory disorder in a patient, the system comprising:
    a respiratory therapy device configured to output usage data;
    a memory containing machine readable medium comprising machine executable code having stored thereon instructions; and
    a control system coupled the memory comprising one or more processors, the control system configured to execute the machine executable code to cause the control system to:
    receive, from the respiratory therapy device, a set of usage data for a therapy session for a patient;
    identify a set of previously stored usage data for the patient within a past time window;
    process the set of usage data and the set of previously stored usage data with an algorithm to determine the likelihood the patient is to reduce usage of the respiratory therapy device within a future time window, the algorithm including a regression model with respective coefficients that scale respective inputs to the regression model to determine the likelihood the patient is to reduce usage, the regression model including a plurality of inputs, the plurality of inputs including an age of the patient and average hours of usage over the past time window;
    output an indication the patient is likely to reduce usage if the likelihood is above a predetermined threshold; and adjust a setting on the respiratory therapy device based at least in part on the likelihood being above the predetermined threshold and an identified issue derived from the usage data;
wherein the respiratory therapy device treats the respiratory disorder of the patient via the adjusted setting, and wherein the likelihood the patient is to reduce usage comprises the likelihood the patient is to reduce usage from a first number of average hours per night to a second number of average hours per night, the second number of average hours per night being non-zero and less than the first number of average hours per night.

2. The system of claim 1, wherein the usage data is output after each time a patient completes a therapy session.

3. The system of claim 1, wherein the usage data comprises total time of use for a session, and date and time stamp data.

4. The system of claim 1, wherein the likelihood the patient is to reduce usage comprises the likelihood the patient is to terminate using the respiratory therapy device.

5. The system of claim 1, wherein the algorithm pre-processes the set of usage data and the set of previously stored usage data to determine non-usage days, the average hours of usage, and standard deviation of hours of usage.

6. The system of claim 5, wherein the algorithm outputs a probability of terminating therapy for the patient.

7. The system of claim 5, wherein the algorithm further pre-processes the set of usage data and the set of previously stored usage data to determine the weekly trend of non-usage days, average hours of usage, and standard deviation of hours of usage.

8. The system of claim 5, wherein the algorithm is a set of logistical regression models each trained using separate prior time windows of training data for a respective one of the logistical regression models to estimate probability of terminating therapy for a respective day in the future time window.

9. The system of claim 1, wherein the indication is an alarm, a notification on a patient mobile device, a notification on a provider computing device, or a notification on a display of the respiratory therapy device.

10. The system of claim 1, wherein the indication comprises instructions sent to a display to depict selectable alternative therapies to the patient comprising at least ramp therapy and wherein each of the alternative therapies are associated with a set of therapy settings for the respiratory therapy device.

11. The system of claim 10, wherein the control system is further configured to:
receive a patient input comprising the patient's selection of the selectable display of alternative therapies, the patient input indicating the identified issue; and
send, to the respiratory therapy device, instructions to change the therapy settings on the respiratory based on the patient input.

12. The system of claim 1, wherein the indication comprises instructions sent to a display to depict selectable alternative patient interfaces to the patient.

13. The system of claim 12, wherein the control system is further configured to:
receive a patient input comprising the patient's selection of the selectable display of alternative patient interfaces; and
send, to a remote external device, instructions to purchase and deliver the patient's selection to the patient.

14. The system of claim 10, wherein the control system is further configured to:
receive a second set of usage data output from the respiratory therapy device;
identify a second set of previously stored usage data for the patient within a second past time window that is equal in length to the first time window;
process the second set of usage data and the second set of previously stored usage data with the algorithm to determine the likelihood the patient is to reduce usage of the respiratory therapy device within a second future time window; and
output an indication the patient is likely to reduce usage if the likelihood is above a predetermined threshold.

15. The system of claim 10, wherein the control system is further configured to:
determine whether usage data has been received in a particular time window; and
if the control system determines no usage data has been received within the time window, store non-usage data referenced to that time window.

16. The system of claim 15, wherein the time window is a 24 hour time period.

17. The system of claim 6, wherein the non-usage data is a non-usage day.

18. The system of claim 1, wherein the algorithm is selected by the control system from a set of algorithms each referenced to a type of respiratory therapy device.

19. The system of claim 1, wherein the algorithm is selected by the control system from a set of algorithms based on the provider of the respiratory therapy device.

20. The system of claim 1, wherein the respiratory therapy device is a CPAP.

21. The system of claim 1, wherein the algorithm is selected based on the demographic information of the patient.

22. The system of claim 1, wherein the plurality of inputs further includes standard deviation of hours of usage over the past time window.

23. The system of claim 22, wherein the plurality of inputs further includes one or more of a number of non-zero days over the past time window, a historical therapy duration measured in number of intervals of the past time window, an engagement with associated online platforms over the past time window, apnea-hypopnea index (AHI) over the past time window, and leak flow rate over the past time window.

24. The system of claim 22, wherein the average hours of usage over the past time window includes average hours of usage over a first portion of the past time window and average hours of usage over a second portion of the past time window, the regression model having different coefficients for the average hours of usage over a first portion of the past time window and the average hours of usage over a second portion of the past time window, and wherein the plurality of inputs further includes the number of non-zero days over the past time window and the historical therapy duration measured as number of intervals of the past time window.

25. A method for treating a respiratory disorder in a patient, the method comprising:
receiving, at a control system comprising one or more processors and output from a respiratory therapy device, a set of usage data for a patient;
identifying, by the control system, a set of previously stored usage data for the patient within a past time window;
pre-processing, by the control system, the set of usage data and the set of previously stored usage data to output a usage feature set;

receiving, by the control system, profile data of the patient comprising the patient's age, a type of respiratory therapy device used by the patient, and the patient's healthcare provider;

selecting, by the control, system, an algorithm based on the profile data;

processing, by the control system, the feature set via the algorithm to determine the likelihood the patient is to reduce usage of the respiratory therapy device within a future time window, the algorithm including a regression model with respective coefficients that scale respective inputs to the regression model to determine the likelihood the patient is to reduce usage, the regression model including a plurality of inputs, the plurality of inputs including an age of the patient and average hours of usage over the past time window;

outputting an indication the patient is likely to reduce usage if the likelihood is above a predetermined threshold; and adjusting a setting on the respiratory therapy device based at least in part on the likelihood being above the predetermined threshold and an identified issue derived from the usage data;

wherein the respiratory therapy device treats the respiratory disorder of the patient via the adjusted setting, and wherein the likelihood the patient is to reduce usage comprises the likelihood the patient is to reduce usage from a first number of average hours per night to a second number of average hours per night, the second number of average hours per night being non-zero and less than the first number of average hours per night.

26. The method of claim 25, wherein the algorithm is a set of models, and each model estimates the probability the patient is likely to reduce usage on a separate day in the future time window and each model in the set of models comprising a machine learning algorithm previously trained using a set of training data from patients with known termination results and from a prior time window starting at the day for which the model estimates the probability a patient will reduce usage of respiratory therapy.

27. The method of claim 25, wherein the algorithm is trained using data from a set of patients that terminated therapy and a set of patients that did not terminate therapy.

28. A non-transitory machine readable medium having stored thereon instructions for performing a method comprising machine executable code which when executed by at least one machine, causes the machine to:

receive, from a respiratory therapy device, a set of usage data for a patient;

retrieve, from a database, profile data of the patient comprising the patient's age, a type of respiratory therapy device used by the patient, and the patient's healthcare provider;

process the set of usage data and the profile data with an algorithm to determine the likelihood the patient is to reduce usage of the respiratory therapy device within a future time window, the algorithm including a regression model with respective coefficients that scale respective inputs to the regression model to determine the likelihood the patient is to reduce usage, the regression model including a plurality of inputs, the plurality of inputs including an age of the patient and average hours of usage over the past time window;

output an indication the patient is likely to reduce usage if the likelihood is above a predetermined threshold; and adjust a setting on the respiratory therapy device based at least in part on the likelihood being above the predetermined threshold and an identified issue derived from the usage data;

wherein the respiratory therapy device treats the respiratory disorder of the patient via the adjusted setting, and wherein the likelihood the patient is to reduce usage comprises the likelihood the patient is to reduce usage from a first number of average hours per night to a second number of average hours per night, the second number of average hours per night being non-zero and less than the first number of average hours per night.

29. The non-transitory machine readable medium of claim 28, wherein the usage data comprises therapy settings.

30. The non-transitory machine readable medium of claim 9, wherein the usage data comprises sensor readings output from the respiratory therapy device.

31. A non-transitory machine readable medium having stored thereon instructions for performing a method comprising machine executable code which when executed by at least one machine, causes the machine to:

receive, from a respiratory therapy device, a set of usage data for a patient;

process the set of usage data with an algorithm to determine the likelihood the patient is to reduce usage of the respiratory therapy device within a future time window, the algorithm including a regression model with respective coefficients that scale respective inputs to the regression model to determine the likelihood the patient is to reduce usage, the regression model including a plurality of inputs, the plurality of inputs including an age of the patient and average hours of usage over the past time window;

output an indication the patient is likely to reduce usage if the likelihood is above a predetermined threshold; and adjust a setting on the respiratory therapy device based at least in part on the likelihood being above the predetermined threshold and an identified issue derived from the usage data;

wherein the respiratory therapy device treats a respiratory disorder of the patient via the adjusted setting, and wherein the likelihood the patient is to reduce usage comprises the likelihood the patient is to reduce usage from a first number of average hours per night to a second number of average hours per night, the second number of average hours per night being non-zero and less than the first number of average hours per night.

* * * * *